(12) United States Patent
Futerman et al.

(10) Patent No.: US 7,429,460 B2
(45) Date of Patent: Sep. 30, 2008

(54) METHODS OF SCREENING FOR INHIBITORS OF PHOSPHOLIPID SYNTHESIS RELATED TO GLYCOLIPID-STORAGE DISEASES

(75) Inventors: Anthony H. Futerman, Rehovot (IL); Jacques Bodennec, Lesneven (FR); Dori Pelled, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 898 days.

(21) Appl. No.: 10/342,311

(22) Filed: Jan. 15, 2003

(65) Prior Publication Data

US 2004/0137531 A1 Jul. 15, 2004

(51) Int. Cl.
G01N 33/567 (2006.01)
C12Q 1/48 (2006.01)
C12N 9/99 (2006.01)
C12N 9/10 (2006.01)

(52) U.S. Cl. .................. 435/7.21; 435/15; 435/184; 435/193

(58) Field of Classification Search .............. 435/15, 435/193, 7.1, 7.21, 184, 4; 514/1
See application file for complete search history.

(56) References Cited

U.S. PATENT DOCUMENTS 5,744,461 A * 4/1998 Hostetler et al. ............ 514/141

FOREIGN PATENT DOCUMENTS

WO  WO 00/62779  10/2000

OTHER PUBLICATIONS

Buccoliero et al. "The Role of Sphongolipids in Neuronal Development: Lessons from Models of Sphingolipid Storage Diseases," Neurochemical Res. (Aug. 2002) 27 (7/8): 565-574.*
Raas-Rothschild et al. "Glycosphingolipidoses: Beyond the enzymatic defect" Glycoconjugate Journal (2004) 21(6): 295-304.*
Song et al. "Hydrolysis of exogenous [3H]phosphatidylcholine by brain membranes and cytosol" Neurochem. Res. (1993) 18(12): 1305-1311.*
Bodennec et al. "Photphatidylcholine synthesis is elevated in neuronal models of Gaucher disease due to direct activation of CTP-:phosphocholine cytidylyltransferase by glucosylceramide" The FASEB Journal (2002; published on-line Sep. 5, 2002) 16:1814-1816.*
Platt et al. "Inhibition of substrate synthesis as a strategy for glycolipid lysosomal storage disease therapy" J. Inherit. Metab. Dis. (2001) 24: 275-290.*
Abe Akir, et al., "Induction of glucosylceramide synthase by synthase inhibitors and ceramide", Biochimica et Biophysica Acta, vol. 1299, pp. 333-341 (1996).
D. Ardail et al., "Occurence Of Ceramides And Neutral Glycolipids With Unusual Long-Chain Base Composition In Purified Rat Liver Mitochondria", FEBS Letters, vol. 488, pp. 160-164 (2001).

Rebecca S. Arnold et al., "Lipid Regulation of CTP:Phosphocholine Cytidylyltransferase: Electrostatic, Hydrophobic, and Synergistic Interactions of Anionic Phospholipids and Diacylglycerol", Biochemistry, vol. 35, pp. 9917-9924 (1996).
Noman W. Barton et al., "Therapeutic Reponse To Intravenous Infusions Of Glucocerebrosidase In A Patient With Gaucher Disease", Medical Sciences, Proc. Natl. Acad. Sci. USA, vol. 87, pp. 1913-1916, (1990).
Adi B. Brann et al., "Ceramide Signaling Downstream Of The p75 Neurotrophin Receptor Mediates The Effects Of Nerve Growth Factor On Outgrowth Of Cultured Hippocampal Neurons", The Journal of Neuroscience, vol. 19, No. 19, pp. 8199-8206 (1999).
Rosemary B. Correll et al., "Modulation Of The Activities Of Enzymes Of Membrane Lipid Metabolism By Non-Bilayer-Forming Lipids", Chemistry And Physics Of Lipids, vol. 81, pp. 215-227 (1996).
Rosemary B. Correll et al., "Regulation Of CTP: Phosphocholine Cytidylytransferase By Amphitropism And Relocalization", TIBS 25, Reviews pp. 441-447, (2000).
S. C. Datta et al., "Stimulation Of Liver Growth And DNA Synthesis By Glucosylceramide", Lipids, vol. 23, pp. 508-510 (1988).
J. C. Dittmer et al., "A Simple, Specific Spray For The Detection Of Phospholipids On Thin-Layer Chromatograms" Notes On Methodology, Journal of Lipid Research, vol. 5, pp. 126-127 (1964).
Anders Erikson et al., "Neuronopathic Forms Of Gaucher's Disease", Baillière's Clinical Haematology, vol. 10, No. 4, pp. 711-723 (1997).
Jordi Folch et al., "A Simple Method For The Isolation And Purification Of Total Lipides From Animal Tissues", (From the McLean Hospital Research Laboratories, Waverley, and the Department of Biological Chemistry, Harvard Medical School, Boston, Massachusetts pp. 497-509 (1956).
Anthony H. Futerman et al., "Determination Of The Intracellular Sites And Topology Of Glucosylceramide Synthesis In Rat Liver", Biochem. J., vol. 280, pp. 295-302 (1991).
Haris Jamil et al., "Evidence That Binding Of CTP: Phosphocholine Cytidlyltransferase To Membranes In Rat Hepatocytes Is Modulated By The Ratio Of Bilayer—To Non-Bilayer-Forming Lipids" Biochem. J., vol. 291, pp. 419-427 (1993).
Claudia Kent, "Eukaryotic Phospholipid Biosynthesis", Annual Reviews, Biochem., vol. 64,pp. 315-343 (1995).
E. Korkotian et al., "Elevation Of Intracellular Glucosylceramide Levels Results In An Increase In Endoplasmic Reticulum Density And In Functional Calcium Stores In Cultured Neurons", Journal of Biological Chemistry, vol. 274, No. 31, pp. 21673-21678, (1999).

(Continued)

*Primary Examiner*—Sandra Saucier
*Assistant Examiner*—Susan Hanley
(74) *Attorney, Agent, or Firm*—Winston & Strawn LLP

(57) ABSTRACT

The present invention discloses methods of screening for identification of compounds that inhibit novel targets in the enzymatic pathway of phospholipid synthesis that are related to glycolipid storage diseases, and use of the compounds for treating patients affected with glycolipid storage diseases, particularly Gaucher disease. Specifically, the compounds of the present invention are intended to inhibit the accumulation of phosphatidylcholine (PC), wherein PC accumulation is increased due to the activation of CTP:phosphocholine cytidylyltransferase (CCT) upon glucosylceramide (GlcCer) accumulation.

7 Claims, 11 Drawing Sheets

OTHER PUBLICATIONS

Gunter Legler et al., "Active Site Directed Inhibition Of A Cytosolic β-Glucosidase From Calf Liver By Bromoconduritol B Epoxide And Bromoconduritol F", Archives of Biochemistry and Biophysics, vol. 260, No. 1, pp. 437-421 (1988).

Athanasios Lykidis et al., "Lipid Activation Of CTP:Phosphocholine Cytidylyltransferase α: Characterization And Identification Of A Second Activation Domain", Biochemistry., vol. 40, pp. 494-503 (2001).

Hamid Morjani et al., "Elevation Of Glucosylceramide In Multidrug-Resistant Cancer Cells And Accumulation In Cytoplasmic Droplets", Int. J. Cancer, vol. 94, pp. 157-165 (2001).

Norman S. Radin et al., Killing Cancer Cells By Poly-Drug Elevation Of Cerarnide Levels A Hypothesis Whose Time Has Come?, Eur. J. Biochem. vol. 268, pp. 193-204 (2001).

Dori Pelled et al., "Death-Associated Protein (DAP) Kinase Plays A Central Role Inceramide-Induced Apoptosis In Cultured Hippocampal Neurons", Journal of Biological Chemistry, vol. 277, No. 3, pp. 1957-1961, (2002).Dori Pellef et al., The Increased Sensitivity Of Neurons With Elevated Gluococerebroside To Neurotoxic Agents Can Be Reversed By Imiglucerase, J. Inherit. Metab. Dis., vol. 23, pp. 175-184 (2000).F. M. Platt et al., "N-Butyldeoxygalactonojirimycin Inhibits Glycolipid Biosynthesis But Does Not Affect N-Linked Oligosaccharide Processing", Journal of Biological Chemistry, vol. 269, No. 43, pp. 27108-27114, (1994).Norman S. Radin et al., "Chemotherapy by Slowing Glucosphingolipid Synthesis", Biochemical Pharmacology, vol. 57, pp. 589-595, (1999).

Dori Pelled et al., The Increased Sensitivity Of Neurons With Elevated Glucocerebroside To Neurotoxic Agents Can Be Reversed By Imiglucerase, J. Inherit. Metab. Dis., vol. 23, pp. 175-184 (2000).

F. M. Platt et al., "N-Butyldeoxynojirimycin Is A Novel Inhibitor Of Glycolipid Biosynthesis", Journal of Biological Chemistry, vol. 269, No. 11, pp. 8362-8365, (1994).F. M. Platt et al., "N-Butyldeoxygalactonojirimycin Inhibits Glycolipid Biosynthesis But Does Not Affect N-Linked Oligosaccharide Processing", Journal of Biological Chemistry, vol. 269, No. 43, pp. 27108-27114, (1994). Norman S. Radin et al., "Chemotherapy by Slowing Glucosphingolipid Synthesis", Biochemical Pharmacology, vol. 57, pp. 589-595, (1999).

F. M. Platt et al., "N-Butyldeoxynojirimycin Is A Novel Inhibitor Of Glycolipid Biosynthesis", Journal of Biological Chemistry, vol. 269, No. 11, pp. 8362-8365, (1994).F. M. Platt et al., "N-Butyldeoxygalactonojirimycin Inhibits Glycolipid Biosynthesis But Does Not Affect N-Linked Oligosaccharide Processing", Journal of Biological Chemistry, vol. 269, No. 43, pp. 27108-27114, (1994).

Norman S. Radin et al., "Chemotherapy by Slowing Glucosphingolipid Synthesis", Biochemical Pharmacology, vol. 57, pp. 589-595, (1999).

F. M. Platt et al., "N-Butyldeoxygalactonojirimycin Inhibits Glycolipid Biosynthesis But Does Not Affect N-Linked Oligosaccharide Processing", Journal of Biological Chemistry, vol. 269, No. 43, pp. 27108-27114, (1994).Norman S. Radin et al., "Chemotherapy by Slowing Glucosphingolipid Synthesis", Biochemical Pharmacology, vol. 57, pp. 589-595, (1999).

Norman S. Radin et al., "Chemotherapy by Slowing Glucosphingolipid Synthesis", Biochemical Pharmacology, vol. 57, pp. 589-595, (1999).

J. S. Sanghera et al., "CTP:Phosphocholaine Cytidylyltransferase Is a Substrate for cAMP-Dependent Protein Kinase in Vitro", Journal of Biological Chemistry, vol. 264, No. 15, pp. 1215-1223, (1989).

Andreas Schwarz et al., "Distinct Rotes For Ceramide And Glucosylceramide At Different Stages Of Neuronal Growth", Journal of Neuroscience, vol. 17, No. 9, pp. 2929-2938, (1997).

Andreas Schwarz et al., "A Regulatory Role for Sphingolipids in Neuronal Growth Inhibition Of Sphingolipid Synthesis And Degradation Have Opposite Effects On Axonal Branching", Journal of Biological Chemistry, vol. 270, No. 18, pp. 10990-10998, (1995).

P. S. Sohal et al., "Sphingosine Inhibits The Activity Of Rat Liver CTP:Phosphochoine Cytidylyltransferase", Journal of Biological Chemistry, vol. 265, No. 20, pp. 11746-11750, (1990).

V. L. J. Tybulewicz et al., "Animal Model Of Gaucher's Disease From Targeted Disruption Of The Mouse Glucocerebrosidase Gene", Nature, vol. 357, pp. 407-410 (1992).

G. Vielhaber et al., "Localization Of Ceramide And Glucosylceramide In Human Epidermis By Immunogold Electron Microscopy", The Journal Investigative Dermatology, vol. 117, No. 5, pp. 1126-1136 (2001).

P. A. Weinhold et al., "Choline-Phosphate Cytidylyltransferase", Methods In Enzymology, vol. 209, pp. 248-258.

P. A. Weinhold et al., "The Purification and Characterization of CTP:Phosphoryleholine Cytidylyltransferase From Rat Liver", Journal of Biological Chemistry, vol. 261, No. 15, pp. 5104-5110, (1986).

G. Y. Wu et al., "Receptor-Mediated In Vitro Gene Transformation By A Soluble DNA Carrier System", Journal of Biological Chemistry, vol. 262, No. 10, pp. 4429-4432, (1987).

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: artificial
<220> FEATURE:
<223> OTHER INFORMATION: unknown

<400> SEQUENCE: 1
cttgggtgga gaggctattc                                              20

<210> SEQ ID NO 2
<211> LENGTH: 20
<212> TYPE: DNA
<213> ORGANISM: artificial
<220> FEATURE:
<223> OTHER INFORMATION: unknonw

<400> SEQUENCE: 2
aggtgagatg acaggagatc                                              20

<210> SEQ ID NO 3
<211> LENGTH: 20
<212> TYPE: DNA
<213> ORGANISM: artificial
<220> FEATURE:
<223> OTHER INFORMATION: unknown

<400> SEQUENCE: 3
caaatgttgc ttgtctggtg                                              20

<210> SEQ ID NO 4
<211> LENGTH: 20
<212> TYPE: DNA
<213> ORGANISM: artificial
<220> FEATURE:
<223> OTHER INFORMATION: unknown

<400> SEQUENCE: 4
gtcagtcgag tgcacagttt                                              20

<210> SEQ ID NO 5
<211> LENGTH: 25
<212> TYPE: DNA
<213> ORGANISM: artificial
<220> FEATURE:
<223> OTHER INFORMATION: unknown

<400> SEQUENCE: 5
gaaccctcct ttaccacgta actgg                                        25

<210> SEQ ID NO 6
<211> LENGTH: 20
<212> TYPE: DNA
<213> ORGANISM: artificial
```

```
<220> FEATURE:
<223> OTHER INFORMATION: unknown

<400> SEQUENCE: 6
gatgccagcc acctaacacg                                                    20

<210> SEQ ID NO 7
<211> LENGTH: 20
<212> TYPE: DNA
<213> ORGANISM: artificial
<220> FEATURE:
<223> OTHER INFORMATION: unknown

<400> SEQUENCE: 7
actttagtaa gccctatgtc                                                    20

<210> SEQ ID NO 8
<211> LENGTH: 20
<212> TYPE: DNA
<213> ORGANISM: artificial
<220> FEATURE:
<223> OTHER INFORMATION: unknown

<400> SEQUENCE: 8
gatgatgtct gatgtggaga                                                    20

<210> SEQ ID NO 9
<211> LENGTH: 20
<212> TYPE: DNA
<213> ORGANISM: artificial
<220> FEATURE:
<223> OTHER INFORMATION: unknown

<400> SEQUENCE: 9
tgaaaaactg accattgctc                                                    20

<210> SEQ ID NO 10
<211> LENGTH: 20
<212> TYPE: DNA
<213> ORGANISM: artificial
<220> FEATURE:
<223> OTHER INFORMATION: unknown

<400> SEQUENCE: 10
acaattctgg tgatgatgtc                                                    20

<210> SEQ ID NO 11
<211> LENGTH: 19
<212> TYPE: DNA
<213> ORGANISM: artificial
<220> FEATURE:
<223> OTHER INFORMATION: unknown

<400> SEQUENCE: 11
ttagcacccc tggccaagg                                                     19

<210> SEQ ID NO 12
<211> LENGTH: 20
<212> TYPE: DNA
<213> ORGANISM: artificial
<220> FEATURE:
<223> OTHER INFORMATION: unknown

<400> SEQUENCE: 12
attactcctt ggaggccatg                                                    20
```

METHODS OF SCREENING FOR INHIBITORS OF PHOSPHOLIPID SYNTHESIS RELATED TO GLYCOLIPID-STORAGE DISEASES

FIELD OF THE INVENTION

The present invention relates in general to the field of glycolipid storage diseases, more particularly to methods of screening for drugs for the treatment of glycolipid storage diseases, specifically for compounds that inhibit deleterious phospholipid synthesis.

BACKGROUND OF THE INVENTION

In humans, a number of inherited disorders occur in lysosomal sphingolipid catabolism (commonly known as "sphingolipidoses"). For example, an inherited deficiency of the lysosomal sphingomyelinase underlies Niemann-Pick disease, and defective activity of the lysosomal ceramidase causes Farber disease. The most frequently encountered disorder of sphingolipid catabolism is Gaucher disease (Barranger J A and Ginns E I.1989. Glucosylceramide lipidoses: Gaucher's disease. In: The Metabolic Basis of Inherited Diseases. C R Scriver, A L Beaudent, W S Sly & D Valle, Eds. McGraw-Hill Inc. New York, 1677-1698). The metabolic basis of this disorder is a deficiency in activity of the catabolic beta-glucosidase enzyme, glucocerebrosidase (E.C.3.2.1.45), which catalyzes the hydrolysis of glucosylceramide (glucocerebroside) to glucose and ceramide.

In patients with Gaucher disease glucosylceramide (GlcCer) accumulates in tubular aggregates, in particular in lysosomes of macrophages. The lipid-laden macrophages have a typical morphology and are usually referred to as "Gaucher cells". In the course of clinical manifestation of Gaucher disease the abnormal macrophages may accumulate in large quantities in various body locations, such as the bone marrow compartment, spleen, liver, kidney, and lungs. The most pronounced clinical symptoms associated with Gaucher disease are progressive splenomegaly, hepatomegaly, and skeletal deterioration. Most Gaucher disease patients do not develop neurological complications. The common non-neuronopathic form of the disease is called Type 1 Gaucher disease. In very severe cases of Gaucher disease characteristic neurological abnormalities may also occur, resulting in lethal complications at infantile (Type 2) or juvenile (Type 3) stages of development.

In recent years, several therapies have been proposed for the treatment of Gaucher disease. Since 1990 an effective therapeutic intervention for Gaucher disease is available, based on the chronic supplementation of patients with human glucocerebrosidase (Barton N W Furbish F S Murray G J Garfield M Brady R O.1990. Therapeutic response to intravenous infusion of glucocerebrosidase in a patient with Gaucher disease. Proc Natl Acad Sci USA 87:1913-1916). Glucocerebrosidase isolated from human placenta (U.S. Pat. No. 3,910,822) was the first source for a commercial form of glucocerebrosidase replacement therapy (CEREDASE®, produced by Genzyme Corp.). Later commercial production for enzyme replacement therapy included CEREZYME®, a recombinant enzyme produced in CHO cells, also by Genzyme Corp. (U.S. Pat. Nos. 5,236,838; and 5,549,892). U.S. Pat. Nos. 5,879,680 and 6,074,684 disclose cloned DNA for synthesizing human glucocerebrosidase. Conjugates of the glucocerebrosidase enzyme with polyethylene glycol (PEG) have also been proposed by Enzon Inc. for treatment of Gaucher's disease (see for example U.S. Pat. Nos. 5,705,153 and 5,620,884).

The most pronounced beneficial effects of enzyme replacement therapy are the reduction in liver and spleen volumes, and the improvements in hematological parameters such as hemoglobulin concentration and thrombocyte and leukocyte counts. However, marked inter-individual differences exist in the rate and extent of clinical response, even among related patients that are treated with the same dosing regimen. In general, the most marked clinical improvements occur within the first year of treatment, accompanied by a pronounced correction of biochemical serum abnormalities. A complete reversal of clinical signs and complete normalization of serum abnormalities, such as elevated levels of angiotensin converting enzyme, tartrate-resistant acid phosphatase and chitotriosidase, is not achieved by enzyme therapy, not even in the case of patients that receive high doses of glucocerebrosidase for a number of years. In addition, the costs associated with successful enzyme replacement therapy have hitherto been exceptionally high, so that enzyme therapy of Gaucher disease is one of the most expensive drug treatments for any disease. Notably, although the glucocerebrosidase enzyme preparation is known to contain minor amounts of human chorionic gonadotropin (HCG) and other impurities, the experience so far indicates that enzyme therapy is safe.

Another approach for treatment of the disease is gene therapy. In general, pluripotent hematopoietic stem cells are isolated and transduced with a vector containing human glucocerebrosidase cDNA. The transduced cells are then transplanted into a Gaucher disease patient to provide therapeutically effective levels of glucocerebrosidase activity. For example, U.S. Pat. No. 5,911,983 discloses methods for transplantation of hematopoietic stem cells comprising retroviral vectors which express the glucocerebrosidase gene into a Gaucher disease patient, to provide therapeutically effective levels of glucocerebrosidase activity. U.S. Pat. No. 6,066,626 discloses vectors comprising a transgene encoding a biologically active human lysosomal enzyme, wherein such vector enables sustain expression of the biologically active enzyme in mammalian cells.

An additional recent approach for the treatment of Gaucher disease is the so called "substrate deprivation therapy". According to this approach a marked reduction in the synthesis of GlcCer may have a beneficial effect because the amount of GlcCer that has to be degraded by macrophages would be lower. Several inhibitors of GlcCer synthase have been developed, e.g. 1-phenyl-decanoylamino-3-morpholino-1-propanol (PDMP) and its analogue 1-phenyl-2-hexadecanoylamino-3-morpholino-1-propanol (PPMP) (Abe A Radin N S Shayman A. 1996. Induction of glucosylceramide synthase by synthase inhibitors and ceramide Biochim. Biophys. Acta 1299:333-341), butyl-deoxynojirimycin (Platt F M Neises G R Dwek R A Butters T D. 1994. N-butyldeoxynojirimycin is a novel inhibitor of glycolipid biosynthesis J Biol Chem 269:8362-8365) and butyl-deoxygalactonojirimycin (Platt F M Neises G R Karlsson G B Dwek R A Butters T D. 1994. N-butyldeoxygalactonojirimycin inhibits glycolipid biosynthesis but does not affect N-linked oligosaccharide processing. J Biol Chem 269:27108-27114; U.S. Pat. Nos. 5,472, 969; 5,786,368; 5,798,366; and 5,801,185).

A disadvantage of the "substrate deprivation" approach is that a priori not only the synthesis of GlcCer but also that of more complex glycosphingolipids is inhibited. Moreover, the presently available inhibitors of GlcCer synthase are known to exert a number of important biological effects that may limit their applicability as therapeutic agent. For example, PDMP is known to induce apoptosis in some cell types. Butyl-deoxynojirimycin is known to inhibit also the lysosomal glucocerebrosidase and the α-glucosidase I, an ER enzyme that plays a critical role in trimming of N-linked glycans in newly formed glycoproteins, and as such in quality control of protein folding. The antiviral action of butyldeoxynojirimycin may be due to its inhibitory effect on glycoprotein modification. Moreover, it was recently reported that GlcCer synthase inhibitors induce the synthesis of the enzyme. Consequently, these inhibitors would need to be chronically administered to Gaucher patients since their withdrawal would be followed by an abnormally high level of GlcCer synthase activity and increased load of GlcCer.

U.S. Pat. No. 6,177,447 discloses the use of deoxynojirimycin derivatives as glucosylceramidase inhibitors, suggesting that glucosylceramidase activity stimulates activation of macrophages, and therefore specific inhibition of the enzyme activity would prevent further release of pathogenetic factors and disrupt the pathological cascade, resulting in therapeutic effect.

Still another treatment approach is the combination drug therapy, in which typically two of the above described therapies, for example, enzyme replacement and substrate deprivation therapy are combined (for example, U.S. patent application Ser. Nos. 2001/0,044,453; 2002/0,127,213; International Patent Application WO 00/62779).

Juvenile (Type 3) Gaucher patients were successfully treated by bone marrow transplantation. The introduction of the normal genetic information for glucocerebrosidase in hematopoietic stem cells results in the formation of blood cells able to hydrolyze GlcCer at normal rates. Unfortunately, the applicability of bone marrow transplantation as treatment for Gaucher disease is quite restricted due to the limited availability of bone marrow from matched donors and the considerable morbidity associated with this intervention, particularly in the case of adults.

In summary, all the above-described therapies attempt only to overcome the defective activity of the enzyme glucocerebrosidase. This is also true for other glycolipid storage diseases, wherein similar therapeutic approaches are undertaken to overcome the defective activity of the aberrant catabolic enzyme (for example, U.S. Pat. Nos. 6,465,488; 6,066,626; U.S. patent application Ser. No. 2002/0142985).

Thus, there is a recognized need for, and it would be highly advantageous to have alternative targets for novel drug therapies, wherein such therapies may be used alone or in conjunction with the existing treatments of glycolipid storage diseases.

SUMMARY OF THE INVENTION

The present invention is related to the field of glycolipid storage diseases. In particular, the present invention relates to methods of screening for identification and use of new compounds that inhibit novel targets in the enzymatic pathway of phospholipid synthesis that are related to glycolipid-storage diseases, particularly to Gaucher disease.

The present invention is based in part on the finding that accumulation of glucosylceramide (GlcCer) directly activates the rate-limiting enzyme of phosphatidylcholine (PC) synthesis, CTP:phosphocholine cytidylyltransferase (CCT).

Therapies for Gaucher disease hitherto have been developed to target the non-functional or dysfunctional enzyme glucocerebrosidase, and to some extent target directly the accumulation of GlcCer. Although enzyme replacement therapy has proven to be fairly efficient, its effectiveness is reduced over time, and this drug is very expensive.

The methods of the present invention, directed to targets downstream or distal to the dysfunctional glucocerebrosidase, opens the way for the discovery of new drug therapies for the treatment of Gaucher as well as other glycolipid-storage diseases.

According to one aspect the present invention discloses and utilizes a newly identified cascade of biochemical events leading to changes in the growth pattern of cells, specifically neuronal cells and macrophages, upon GlcCer accumulation. Based on these findings the present invention provides novel targets for compounds that can serve as drugs in the treatment of glycolipid storage diseases, specifically Gaucher disease.

According to one embodiment the compounds of the present invention are intended to inhibit the synthesis of phosphatidylcholine (PC), wherein PC synthesis is increased due to the activation of CTP:phosphocholine cytidylyltransferase (CCT) upon GlcCer accumulation.

According to another embodiment, the compounds of the present invention are aimed at inhibiting CCT activity.

According to one currently preferred embodiment, the compounds of the present invention are designed to inhibit the synthesis of neuronal PC stimulated by GlcCer accumulation.

According to another currently preferred embodiment the compounds the compounds of the present invention are designed to inhibit the GlcCer-stimulated synthesis of PC in brain neurons.

According to yet further currently preferred embodiment, the compounds of the present invention are designed to inhibit the synthesis of PC stimulated by GlcCer accumulation in Gaucher cells.

According to another aspect the present invention provides methods of screening for compounds modulating the phospholipid synthesis associated with glycolipid-storage disease, specifically with Gaucher disease.

According to one embodiment the present invention provides a method of screening for a compound that inhibits deleterious effects due to GlcCer activated PC accumulation related to glycolipid storage diseases, the method comprising the steps of:

a. providing a cell culture in which the cells are over expressing GlcCer;

b. exposing the cell culture to at least one candidate compound; and c. measuring the synthesis of PC in the cell culture, wherein a significant decrease in the synthesis of PC as compared to a cell culture incubated without the candidate compound identifies said candidate compound as an inhibitor of PC accumulation; or d. measuring the degradation of PC in the cell culture, wherein a significant increase in the degradation of PC as compared to a cell culture incubated without the candidate compound identifies said candidate compound as an inhibitor of PC accumulation.

The method may further comprise the step of verification of the activity of the compound on the enzymatic activity whether as an isolated enzyme, in cell extracts, in vitro or by any other means as is known in the art.

According to one embodiment, the cell culture is a neuronal cell culture.

According to another embodiment, the cell culture is a macrophage culture.

According to one embodiment, the compound inhibits PC accumulation by inhibiting its synthesis.

According to another embodiment, the compound inhibits PC synthesis by inhibiting the activation of CCT by GlcCer.

According to yet another embodiment the compound inhibits PC synthesis by direct inhibition of CCT.

According to another aspect the present invention provides a pharmaceutical composition comprising as an active ingredient a compound that inhibits PC accumulation by inhibiting CCT activation by GlcCer.

According to one embodiment, the present invention provides a pharmaceutical composition comprising as an active ingredient at least one compound identified by a screening method comprising the steps of:
a. providing a cell culture in which the cells are over expressing GlcCer;
b. exposing the cell culture to at least one candidate compound; and
c. measuring the synthesis of PC in the cell culture, wherein a significant decrease in the synthesis of PC as compared to a cell culture incubated without the candidate compound identifies said candidate compound as an inhibitor of PC accumulation; or
d. measuring the degradation of PC in the cell culture, wherein a significant increase in the degradation of PC as compared to a cell culture incubated without the candidate compound identifies said candidate compound as an inhibitor of PC accumulation,
further comprising a pharmaceutically acceptable diluent, carrier or excipient.

According to one embodiment, the pharmaceutical composition comprises a compound that reduces PC accumulation by inhibition of its synthesis.

According to another embodiment, the pharmaceutical composition comprises a compound that reduces PC synthesis by inhibiting the activation of CCT by GlcCer.

According to yet another embodiment the pharmaceutical composition comprises a compound that reduces PC synthesis by direct inhibition of CCT.

According to one embodiment, the pharmaceutical composition comprises as an active ingredient a glycosphingolipid compound having general formula I:

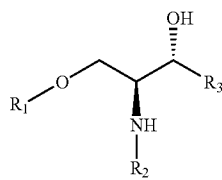

wherein $R_1$ represents a carbohydrate moiety of one to three hexoses selected from the group consisting of uronic acid, glucose, galactose, mannose, glucosamine and galactosamine; and $R_2$ is H, or a straight chain or branched, saturated or unsaturated, substituted or unsubstituted hydrocarbon chain selected from the group consisting of alkyl that may include a cycloalkyl group, alkenyl and alkynyl;

$R_3$ represents a sphingoid moiety comprising 4-25 carbons and unsaturated derivatives thereof; and a pharmaceutically acceptable diluent, carrier or excipient.

In currently preferred embodiments $R_3$ is a sphingoid moiety of 4-18 carbons, and unsaturated derivatives thereof.

As used herein, a glycosphingolipid is a carbohydrate-containing derivative of a sphingoid or ceramide, wherein the carbohydrate residue is attached by glycosidic linkage to O-1 of the sphingoid. As used herein, sphingoids are long-chain aliphatic amino alcohols. Unsaturated derivatives of sphingoids are defined in terms of the location and configuration of each olefinic center.

According to one currently preferred embodiment, the pharmaceutical composition comprises glucosylsphingosine.

According to another currently preferred embodiment the present invention comprises galactosylsphingosine.

According to yet another aspect the present invention provides methods for the treatment of glycolipid storage diseases, particularly Gaucher disease, via inhibition of phospholipid synthesis associated with such diseases.

According to one embodiment the present invention provides a method for treating a patient affected with a glycolipid storage disease comprising the step of administering to said patient a therapeutically affective amount of a compound that inhibits deleterious effects due to GlcCer activated PC accumulation.

According to one embodiment, the glycolipid storage disease is Gaucher disease. The methods of the present invention are suitable for the treatment of all types of Gaucher disease, namely the common Type 1 Gaucher disease, and also the more severe Types 2 and 3.

According to another embodiment, the method of the present invention is administered in combination with at least one additional glycolipid-storage-disease therapy.

According to one currently preferred embodiment, the additional therapy is enzyme replacement therapy.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will be better understood in relation to the description that follows and the drawings in which:

FIG. 5A describes rat hippocampal neurons treated with (stripped bars) or without (black bars) 500 μM CBE. Data are mean ±SEM from 3-6 individual cover slips from 2 separate neuronal cultures. Statistical differences from control neurons are indicated (** p<0.001). FIG. 5B describes hippocampal neurons treated with or without 50 μM PDMP. Data are mean ±SD from 15 individual cover slips. Statistical differences from control neurons are indicated (* p<0.01).

FIG. 6A shows the results of RT-PCR performed with RNA extracted from neurons treated with or without 500 μM of CBE for the indicated times. FIG. 6B shows the results of RT-PCR performed with RNA extracted from Gba neurons on day 4 in culture. FIG. 6C shows a Western blotting performed on Gba brain homogenates using anti-CCTα and anti-CCTβ1/2 antibodies. Each experiment was repeated 2-3 times with similar results.

FIG. 9A shows the elution profile of CCT and of protein from the DEAE-sepharose CL-B6 column, and FIG. 9B the elution profile from the hydroxypatite column. FIG. 9C shows a silver stained gel in which two major bands are observed at Mr~45-50 and 80 KDa. The two right lanes show Western blots of purified CCT using the anti-αCCT and the anti-$β_{1/2}$ CCT.

DETAILED DESCRIPTION OF THE PREFERRED EMBODIMENTS

Figure 1:
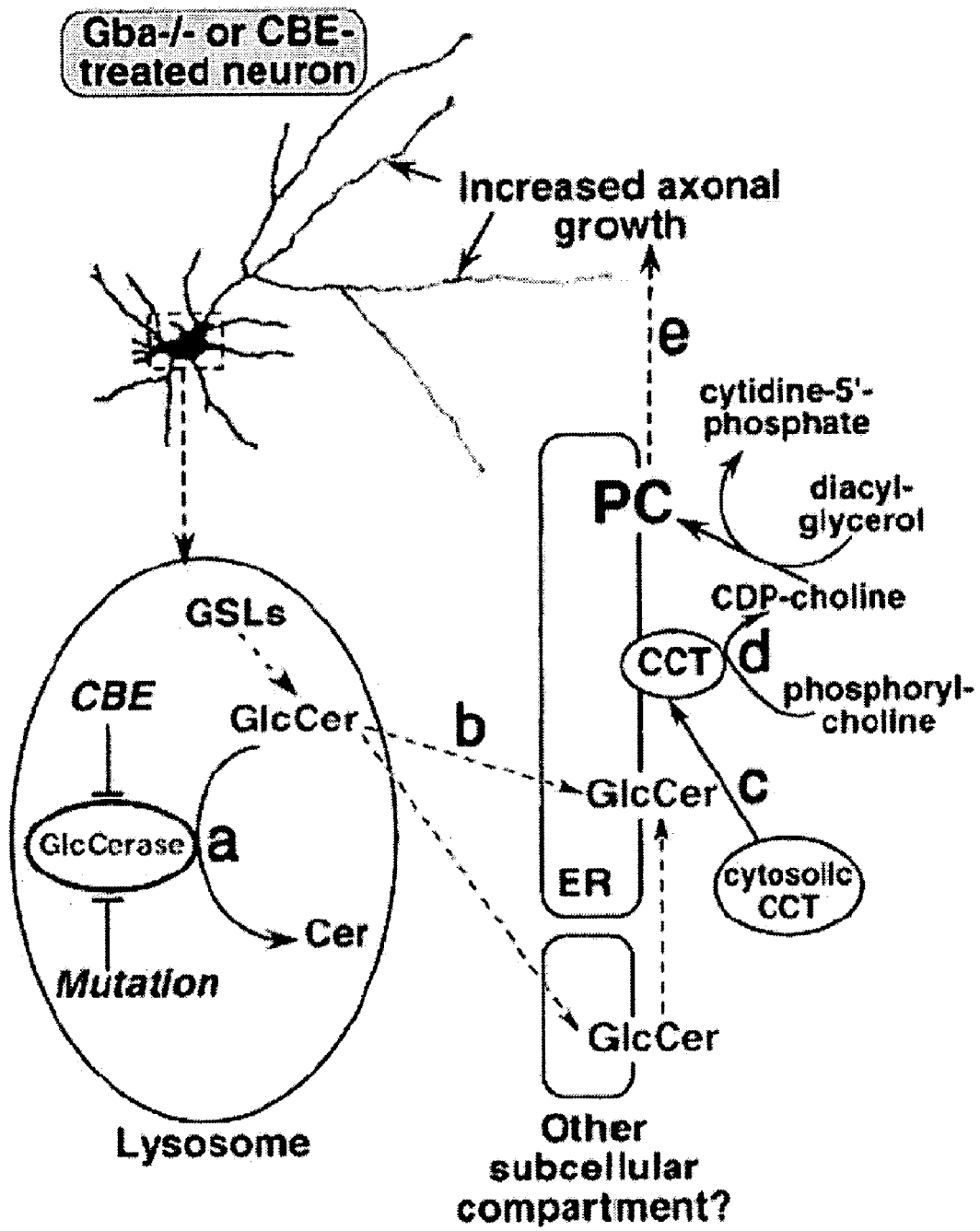
FIG. 1 illustrates the cascade of events lading to deleterious PC accumulation and increased axonal growth.

Currently, the most common therapy for glycolipid storage diseases is enzyme replacement therapy, which involves very high costs and was shown to vary in efficiency from one patient to the next and in the same patient over the course of treatment. Other therapeutic alternatives are suitable only for a limited number of cases (bone marrow transplantation) or have not been yet reduced to practice (gene therapy and substrate deprivation). The present invention is therefore targeted to novel options for therapeutic intervention that may be used by itself or in combination with the existing or proposed therapies, especially with enzyme replacement therapy.

Identification of Novel Targets for Therapeutic Intervention

The present invention proposes targets for intervention downstream to the aberrant enzyme glucocerebrosidase, and its direct outcome, i.e., the accumulation of GlcCer. The novel targets are distal to the defective enzyme itself, and may be beneficially treated alone or in conjunction with enzyme replacement regimens.

The present invention discloses for the first time a cascade of events leading to deleterious phospholipid accumulation, which is one of the phenomena related to glycolipid storage diseases, specifically to Gaucher disease.

The various phenotypic changes related to Gaucher disease are due to the accumulation of Glucosylceramide (GlcCer). One of the inventors of the present invention has previously shown that rat hippocampal neurons treated with conduritol-B-epoxide (CBE), an active site directed irreversible inhibitor of glucoscerebrosidase, show a significant increase in the rate of axonal growth (Schwarz A Rapaport E Hirschberg K and Futerman A H. 1995. A regulatory role for sphingolipids in neuronal growth: inhibition of sphingolipid synthesis and degradation have opposite effects on axonal branching. J Biol Chem 270:10990-10998). In addition, an increase in endoplasmic reticulum (ER) density, and enhanced levels of calcium release from intracellular (probably ER) stores was also observed. The accumulation of GlcCer in these cultures caused enhanced sensitivity to neurotoxic agents (Pelled D Shogomori H and Futerman A H. 2000. The increased sensitivity of neurons with elevated glucocerebroside to neurotoxic agents can be reversed by imiglucerase. J Inherit Metab Dis 23:175-184).

It is now shown for the first time that similar to CBE-treated rat neurons, cultured hippocampal neurons from a mouse model of Gaucher disease (The Gba−/− mouse) exhibit significantly longer axons and more axonal branch points than wild type (Gba+/+) neurons. The present invention further shows that this accelerated axonal growth accompanies the accumulation of GlcCer. The increased growth rates upon intracellular GlcCer accumulation might result in, or be caused by, increased rates of phospholipid synthesis, since phospholipids are the major structural components of membranes and are required for axonal growth.

Indeed, as exemplified herein below, an increase in choline-containing lipids, mainly phosphatidylcholine (PC), was observed in CBE-treated as well as in Gba−/− neuronal cultures. Moreover, the present invention discloses that this PC accumulation is due to an increase in PC synthesis, which, in turn, is due to a direct activation of CCT, the rate-limiting enzyme in PC synthesis, by GlcCer. The same phenomenon was observed also in human macrophages cultured in the presence of CBE.

Other studies have shown that GlcCer injection into mice stimulates liver growth (Datta S C and Radin N S. 1988. Stimulation of liver growth and DNA synthesis by glucosylceramide. Lipids 23:508-510), and enlargement of mouse brain and liver occurs after injection with CBE (Legler G and Bieberich E. 1988. Active site directed inhibition of a cytosolic beta-glucosidase from calf liver by bromoconduritol B epoxide and bromoconduritol F. Arch Biochem Biophys 260: 437-442). Cultured cells also grow faster when treated with exogenously added GlcCer, and GlcCer synthase is activated during periods of rapid axonal growth in cultured neurons. Together, these data suggest that GlcCer may promote cell growth and/or proliferation (reviewed in Radin N S. 1999. Chemotherapy by slowing glucosphingolipid synthesis. Biochem Pharmacol 57:589-595; Radin N S. 2001 Killing cancer cells by poly-drug elevation of ceramide levels: a hypothesis whose time has come? Eur J Biochem 268:193-204)), although the mechanism by which this occurs is still poorly understood.

The principle finding underlying the present invention is the direct activation of CCT by GlcCer. The activation of CCT is highly specific for GlcCer, since galactosylceramide (GalCer) failed to stimulate CCT activity to any appreciable extent.

The mechanism by which GlcCer activates CCT is at present not known. Three different classes of lipid modulators of CCT activity have been described: anionic phospholipids and fatty acids (class I), neutral lipids with small polar head groups such as mono- and diacylglycerol (class II), and cationic lipids such as lyso-sphingolipids (class III). Negatively charged lipids normally activate CCT whereas cationic lipids inhibit its activity. CCT activation by negatively charged lipids may involve the insertion/intercalation of the M lipid-binding domain of CCT into lipid bilayers, or electrostatic interactions between positive charges within the M domain and negatively charged phospholipids in the lipid bilayer. The action of GlcCer, a neutral lipid, could be due to the perturbation of the regular packing of zwitterionic phospholipids, such as has been observed with monoacylglycerols, diacylglycerol and oleyl alcohol (Cornell R B and Arnold. S. 1996. Modulation of the activities of enzymes of membrane lipid metabolism by non-bilayer-forming lipids. *Chem. Phys. Lipids* 81, 215-227).

Alternatively, the ratio of bilayer- to non-bilayer-forming lipids may be altered, facilitating the intercalation of CCT into the lipid bilayer; it has been shown that upon decreasing the ratio of bilayer to non-bilayer forming lipids, such as when membrane levels of diacylglycerol increase, CCT binding to the membrane is stimulated (Jamil H Hatch G M and Vance D E. 1993. Evidence that binding of CTP:phosphocholine cytidylyltransferase to membranes in rat hepatocytes is modulated by the ratio of bilayer- to non-bilayer-forming lipids. *Biochem J* 291: 419-427).

Finally, without wishing to be bound to a certain mechanism, it is proposed that GlcCer could interact with the second, recently characterized lipid binding domain, wherein neutral and anionic lipids differentially interact with the two lipid binding domains (Lykidis A Jackson P Jackowski S. 2001. Lipid activation of CTP: phosphocholine cytidylyltransferase alpha: characterization and identification of a second activation domain. *Biochemistry* 40:494-503).

Based on the above-described underlying principle, the present invention discloses new targets for drugs that may interfere with the biochemical pathway leading to the increase in PC synthesis, wherein this pathway includes direct activation of CCT by GlcCer.

The intracellular localization of CCT varies between different tissues and for different isoforms of the enzyme. However, since the bulk of PC is synthesized in the endoplasmic reticulum (ER), it is reasonable to assume that a significant fraction of cytosolic CCT is associated with the ER, or becomes associated with the ER upon stimulation. In contrast, in Gaucher disease, GlcCer is believed to accumulate in lysosomes. This implies that GlcCer must exit lysosomes so as to interact with CCT. GlcCer is not normally associated with the ER, as it is made distal to the ER (in the Golgi apparatus; Futerman, A H Pagano R E. 1991. Determination of the intracellular sites and topology of glucosylceramide synthesis in rat liver. *Biochem J* 280:295-302). Nevertheless, GlcCer has been detected in the inner membrane of rat liver mitochondria (Ardail D Popa I Alcantara K Pons A Zanetta J P Louisot P Thomas L Portoukalian J. 2001. Occurrence of ceramides and neutral glycolipids with unusual long-chain base composition in purified rat liver mitochondria. *FEBS Letters* 488:160-164), in cytoplasmic droplets (Morjani H Aouali N Belhoussine R Veldman R J Levade T Manfait M. 2001. Elevation of glucosylceramide in multidrug-resistant cancer cells and accumulation in cytoplasmic droplets. *Int J Cance*. 94:157-165), and in trans-Golgi network-like structures (Vielhaber G Pfeiffer S Brade L Lindner B Goldmann T Vollmer E Hintze U Wittern H-P and Wepf R. 2001. Localization of ceramide and glucosylceramide in human epidermis by immunogold electron microscopy. *J Clin Invest* 117: 1126-1136). The specificity of CCT activation to GlcCer might even suggest that GicCer is a normal physiological regulator of this key enzyme in phospholipid synthesis.

As illustrated in FIG. 1, the cascade of events disclosed according the present invention is that subsequent to its accumulation GlcCer escapes from lysosomes (FIG. 1b) and accumulates in the ER. As a result, CCT is translocated from either the cytosol or the nucleus to the ER membrane (FIG. 1c), where PC synthesis is up regulated (FIG. 1d). Increased PC synthesis may be responsible for accelerated rates of cell growth, particularly the accelerated rate of neuronal growth observed upon neuronal accumulation of GlcCer (FIG. 1e), and also upon the GlcCer accumulation in "Gaucher cells"—the enlarged macrophages characteristic to Gaucher disease.

The present invention is therefore aimed at the screening of compounds that inhibit the synthesis of PC, therefore inhibiting the accelerated cell growth.

According to one embodiment the compounds of the present invention are intended to inhibit the synthesis of phosphatidylcholine (PC), wherein PC synthesis is increased due to the activation of CTP:phosphocholine cytidylyltransferase (CCT) by GlcCer accumulation.

According to another embodiment, the compounds of the present invention are aimed at inhibiting CCT activity.

According to one currently preferred embodiment, the compounds of the present invention are designed to inhibit the synthesis of neuronal PC stimulated by GlcCer accumulation.

According to another currently preferred embodiment the compounds of the present invention are designed to inhibit the GlcCer-stimulated synthesis of PC in brain neurons.

According to yet further currently preferred embodiment, the compounds of the present invention are designed to inhibit the synthesis of PC stimulated by GlcCer accumulation in Gaucher cells.

In all forms of Gaucher disease patients display enlarged spleens and livers, and macrophages, designated as "Gaucher cells", are enlarged due to GlcCer accumulation in the lysosomes. The principle finding of the present invention, namely the direct stimulation of CCT activity by GlcCer, leading to accelerated PC synthesis, may account for the increased rate of cell growth.

There is no direct evidence that neuronal growth and/or development is altered in neuronopathic forms of Gaucher disease. However, some changes in neuronal morphology have been observed, including dilated and distended smooth and rough ER in brains from neuronopathic forms of Gaucher diseases, in the brains of mice fed with CBE, and in cultured neurons treated with CBE, consistent with the observed changes in PC synthesis which occur in the ER. It is probably more than a coincidence that axons from Gba−/−mouse neurons are longer than wild type axons; in contrast, in a mouse model of Sandhoff disease, axons are considerably shorter and rates of phospholipid synthesis are decreased.

Surprisingly, the molecular mechanism leading from lysosomal GlcCer accumulation to neuronal disease in the Gaucher's neuronopathic forms (Types 2 and 3) is not known (Erikson A Bembi B and Schiffmann R. 1997. Neuronopathic forms of Gaucher's disease. In Gaucher's Disease (Zimran, A., Ed) Vol. 10 pp. 711-723, Bailliere Tindall, London). The cascade of events disclosed by the present invention may therefore also help in delineating the biochemical basis of neuronal dysfunction in neuronopathic forms of Gaucher disease.

According to yet another embodiment, the compounds are targeted to inhibit the GlcCer-stimulated synthesis of PC in brain neurons. As exemplified herein below, GlcCer directly activate CCT isolated from brain. The CCT isolated for the first time by the inventors of the present invention from adult rat brain appeared to be a mixture of the CCTα and CCTβ$_2$ isoforms of CCT, with more CCTα than CCTβ$_2$. The activity of both isoforms was activated by GlcCer, leading to the accumulation of PC in brain neurons.

Identification of New Drugs

According to yet another aspect the present invention provides a method of screening for new drugs, particularly for new compounds useful for modulating the phospholipid synthesis associated with a glycolipid-storage disease, specifically with Gaucher disease.

According to one embodiment the present invention provides a method of screening for a compound that inhibits deleterious effects due to GlcCer activated PC accumulation related to glycolipid storage diseases, the method comprising the steps of:

a. providing a cell culture in which the cells are over expressing GlcCer;
b. exposing the cell culture to at least one candidate compound; and
c. measuring the synthesis of PC in the cell culture, wherein a significant decrease in the synthesis of PC as compared to a cell culture incubated without the candidate compound identifies said candidate as an inhibitor of PC accumulation; or
d. measuring the degradation of PC in the cell culture, wherein a significant increase in the degradation of PC as compared to a cell culture incubated without the candidate compound identifies said candidate as an inhibitor of PC accumulation.

The method may further comprise the step of verification of the activity of the compound on the enzymatic activity whether as an isolated enzyme, in cell extracts, in vitro or by any other means as is known in the art.

According to the present invention, GlcCer-stimulated activity of CCT result in an enhanced axonal growth and in the enlargement of macrophages in a genetic model of Gaucher disease. Several other studies have also shown that GlcCer accumulation in non-neuronal tissues is accompanied by cell growth and or cell proliferation. In Gaucher disease, not only macrophages become enlarged, but also the spleen and liver. The present invention shows for the first time that GlcCer directly stimulates CCT activity, and as a result, PC synthesis; this cascade of events may account for the undesired increase in cell growth rates. The present invention therefore provides new targets for drug discovery, wherein compounds capable of inhibiting at least one step in the above-described process are to be used for treating a patient affected with glycolipid storage diseases, specifically for treating a patient affected with Gaucher disease.

According to one embodiment, the cell culture is a neuronal cell culture.

According to another embodiment, the cell culture is a macrophage culture.

According to one embodiment, the compound inhibits PC accumulation by inhibition of its synthesis.

According to another embodiment, the compound inhibits PC synthesis by inhibiting the activation of CCT by GlcCer.

According to yet another embodiment the compound inhibits PC synthesis by direct inhibition of CCT.

The compound screening methods for identification of inhibitor compounds may be used in various modifications, which are well known to one skilled in the art.

According to one embodiment, compounds for screening may be produced by synthetic chemistry or may be natural compounds, individual or in mixtures, pre-selected by an algorithm, compressed libraries and the like. A preferred method of screening is known as High-Throughput Screening (HTS), in which thousands of compounds are screened with the aid of robotics.

Pharmaceutical Compositions

According to another aspect the present invention provides a pharmaceutical composition comprising as an active ingredient a compound that inhibits PC accumulation by inhibition of the activation of CCT.

According to one embodiment, the present invention provides pharmaceutical compositions comprising as an active ingredient at least one compound identified by a screening method comprising the steps of:

a. providing a cell culture in which the cells are over expressing GlcCer;
b. exposing the cell culture to at least one candidate compound; and
c. measuring the synthesis of PC in the cell culture, wherein a significant decrease in the synthesis of PC as compared to a cell culture incubated without the candidate compound identifies said candidate compound as an inhibitor of PC accumulation; or
d. measuring the degradation of PC in the cell culture, wherein a significant increase in the degradation of PC as compared to a cell culture incubated without the candidate compound identifies said candidate compound as an inhibitor of PC accumulation, further comprising a pharmaceutically acceptable diluent, carrier or excipient.

According to one embodiment, the pharmaceutical composition comprises a compound that reduces PC accumulation by inhibition of its synthesis.

According to another embodiment, the pharmaceutical composition comprises a compound that reduces PC synthesis by inhibiting the activation of CCT by GlcCer.

According to yet another embodiment the pharmaceutical composition comprises a compound that reduces PC synthesis by direct inhibition of CCT.

According to one embodiment, the pharmaceutical composition comprises a glycosphingolipid compound having general formula I:

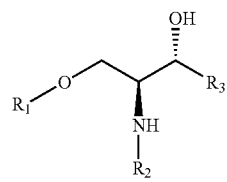

wherein

R$_1$ represents a carbohydrate moiety of one to three hexoses selected from the group consisting of uronic acid, glucose, galactose, mannose, glucosamine and galactosamine; and $R_2$ is H, or a straight chain or branched, saturated or unsaturated, substituted or unsubstituted hydrocarbon chain selected from the group consisting of alkyl that may include a cycloalkyl group, alkenyl and alkynyl;

$R_3$ represents a shingoid moiety comprising 4-25 carbons and unsaturated derivatives thereof; and a pharmaceutically acceptable diluent, carrier or excipient.

In currently preferred embodiments $R_3$ is a sphingoid moiety of 4-18 carbons, and unsaturated derivatives thereof.

As used herein, the term "glycosphingolipid" denotes a carbohydrate-containing derivative of a sphingoid or cermaid, wherein the carbohydrate residue is attached by glycosidic linkage to O-1 of the sphingoid.

The term "sphingoid" denotes a long-chain aliphatic amino alcohol. Unsaturated derivatives of sphingoids are defined in terms of the location and configuration of each olefinic center.

The term "alkyl" denotes branched or unbranched hydrocarbon chains, such as methyl, ethyl, n-propyl, iso-propyl, n-butyl, sec-butyl, iso-butyl, tertbutyl, 2-methylpentyl and octa-decyl.

The term "alkenyl" denotes branched or unbranched hydrocarbon chains containing one or more carbon-carbon double bonds.

The term "alkynyl" denotes branched or unbranched hydrocarbon chains containing one or more carbon-carbon triple bonds.

The term "substituted means that any one or more hydrogen on the designated atom is replaced with a selection from the indicated group, provided that the designated atom's normal valency is not exceeded, and that the substitution results in a stable compound.

Although the number of carbon atoms in $R_2$ is not particularly limited, preferred number resides in a range from 3-20, both ends inclusive. The alkyl, alkenyl and alkynyl groups representing $R_2$ are straight or branched, and both of those substituted with a hydroxyl group, and unsubstituted are allowable. The alkyl group can include in its chain a cycloalkyl group such as cyclopropyl group. There is also no limitation on the position of a double bond in the alkenyl group or a triple bond in the alkynyl group.

According to one currently preferred embodiment, the pharmaceutical composition comprises glucosylsphingosine.

According to another currently preferred embodiment the present invention comprises galactosylsphingosine.

As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to an adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

Various delivery systems are known and can be used to administer the compound of the invention, e.g., encapsulation in liposomes, microparticles, microcapsules, recombinant cells capable of expressing the compound, construction of a nucleic acid as part of a retroviral or other vector, receptor-mediated endocytosis (see, e.g., Wu G Y and Wu C H. 1987. Receptormediated in vitro gene transformation by a soluble DNA carrier system J Biol Chem 262:4429-4432), etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

Therapeutic Use

According to yet further aspect the present invention provides methods for the treatment of glycolipid storage diseases, particularly Gaucher disease. The method is based on the principle finding of the present invention, namely the stimulation of PC synthesis by GlcCer that result in undesired accelerated cell growth. The methods of the present invention may be administered alone or in combination with other therapies for the treatment of glycolipid storage diseases.

According to one embodiment the present invention provides a method for treating a patient affected with glycolipid storage disease comprising the step of administering to said patient a therapeutically affective amount of a compound that reduces deleterious PC accumulation.

According to one embodiment, the method of the present invention is administered in combination with at least one additional glycolipid-storage-disease therapy.

According to one currently preferred embodiment, the additional therapy is enzyme replacement therapy.

According to one embodiment, the glycolipid storage disease is Gaucher disease.

According to one embodiment, the Gaucher disease is Type 1 Gaucher disease.

According to one embodiment, the Gaucher disease is Type 2 Gaucher disease.

According to one embodiment, the Gaucher disease is Type 3 Gaucher disease.

The principles of the invention, the identification of new targets for drugs for the treatment of glycolipid storage diseases according to the present invention may be better understood with reference to the following non limiting examples.

EXAMPLES

Experimental Procedures

Materials

GlcCer, galactosylceramide (GalCer), oleic acid, dioleylphosphatidylcholine (DOPC), choline, phosphorylcholine, CDP-choline, calf thymus DNA, poly-L-lysine, n-octyl-β-D-glucopyranoside, and DEAE-sepharose CL-6B were from Sigma (St. Louis, Mo.). Hydroxyapatite was from Biorad (Hercules, Calif.). CBE and D-threo-1-phenyl-2-decanoyl-amino-3-morpholino-1-propanol (PDMP) were from Matreya (Pleasant Gap, Pa.). Silica gel 60 thin layer chromatography (TLC) plates were from Merck (Darmstadt, Germany). Activated charcoal was from Fluka (Buchs, Switzerland). [$^{14}$C]methyl choline (specific activity 55 mCi/mmol), and [$^{14}$C]methyl phosphorylcholine (specific activity 55 mCi/mmol) were from Amersham (Little Chalfont, UK). Bis-benzimidazole (Hoechst 33342) was from Molecular Probes (Eugene, Oreg.). All solvents were of analytical grade and were purchased from Biolab (Jerusalem, Israel). Anti-CCT antibodies were provided by Dr. S. Jackowski (St Jude Children's Research Hospital, Memphis, Tenn.).

Hippocampal Neurons

Rat (Wistar) or mouse (see below) hippocampal neurons were isolated from day 18 or 17 embryos, respectively, as described (Schwarz A and Futerman, A H. 1997. Distinct roles for ceramide and glucosylceramide at different stages of neuronal growth. J Neurosci 17:2929-2938; Brann A Scott R Neuberger Y Abulafia D Boldin S Fainzilber M and Futerman A H. 1999. Ceramide signaling downstream of the p75 neurotrophin receptor mediates the effects of nerve growth factor on outgrowth of cultured hippocampal neurons. J Neurosci 19, 8199-8206; Pelled D Raveh T Riebeling C Fridkin M Berissi H Futerman A H and Kimchi, A. 2001. Death-associated protein-(DAP) kinase plays a central role in ceramide-induced apoptosis in cultured hippocampal neurons. J Biol Chem 277:1957-1961).

For biochemical analysis, neurons were plated in Neurobasal serum-free medium containing B27 supplements and L-glutamine (Life Technologies Inc., Paisley, UK) at a density of 240,000 cells/24 mm poly-L-lysine-coated glass cover slip. Cytosine β-D-arabinoside (5 µM) was added to the medium on day 2 of culture to prevent glial proliferation. One third of the medium was replaced on day 3 and on day 6.

A breeding pair of a mouse model of Gaucher disease (the Gba mouse; Tybulewicz V L J Tremblay M L LaMarca M E Willemsen R Stubblefield B K Winfield S Zablocka B Sidransky E Martin B M Huang S P Mintzer K A Westphal H Mulligan R C and Ginns E I. 1992. Animal model of Gaucher's disease from targeted disruption of the mouse glucocerebrosidase gene. Nature 357:407-410) was obtained from Jackson laboratories (Bar Harbor, Me.) and bred in the transgenic animal facility of the Weizmann Institute of Science. Since Gba−/−mice do not survive beyond 2 days after birth, heterozygous mice were bred and each individual embryo was genotyped using DNA obtained from either mouse-tails or from the cerebellum, using the Wizard Genomic DNA Purification kit (Promega, Madison, Wis.). Gla knockout mice were identified by PCR by the presence of the neomycin resistance gene (5'-CTTGGGTGGAGAGGCTATTC(SEQ ID NO. 1), 5'-AGGTGAGATGACAGGAGATC)(SEQ ID NO. 2)), the T-cell receptor δ chain as internal control (5'-CAAATGTTGCTTGTCTGGTG, (SEQ ID NO. 3), 5'-GTCAGTCGAGTGCACAGTTT), (SEQ ID NO. 4)), and lack of the wild type 668 nucleotide product from the 9th exon and the 10th intron of murine glucocerebrosidase (5'-GAAC-CCTCCTTTACCACGTAACTGG, (SEQ ID NO. 5), and modified 5'-GATGCCAGCCACCTAACACG(SEQ ID NO. 6)).

Morphological analysis of hippocampal neurons from Gba mice was performed using criteria previously described (Korkotian E Schwarz A Pelled D Schwarzmann G Segal M and Futerman A H. 1999. Elevation of intracellular glucosylceramide levels results in an increase in endoplasmic reticulum density and in functional calcium stores in cultured neurons. J Biol Chem 274:21673-21678), except that images were captured prior to analysis and analyzed using NIH imaging software.

PC Synthesis in Macrophage Cultures

Human macrophages were obtained from healthy donors. Blood samples were immediately diluted 2.5 times with PBS pH 7.4 and layered on 3 ml Ficoll Histopaque 1.077 in conical tubes. The tubes were then centrifuged at 400 g for 25 min. The peripheral blood mononuclear leukocyte (PBL) band at the PBS-plasma/Ficoll interface was taken for further analyses. PBL were washed twice with PBS pH 7.4, and resuspended in 5 ml of RPMI 1640 containing 10% fetal calf serum. An aliquot of the cell suspension was used to assess cell viability using the exclusion trypan-blue test. The cell suspension was adjusted to a final concentration of 6*10$^6$ cells/ml and incubated for 3 hours at 37° C. in a plastic Petri dish (Falcon). Non adherent cell suspension (mononuclear leukocytes) was then transferred to a culture flask while the adherent cells (mainly macrophages) were cultured separately in RPMI 1640 supplemented with 10% fetal calf serum, 2 mM L-glutamine, 100 U/ml penicillin and 0.1 mg/ml streptomycin. The cells were cultured in separate cultures with or without 500 µM CBE for 5 days; on day 5, PMA was added to the macrophage suspension (final concentration: 10 ng/ml) to allow full differentiation. After 24 hours in presence of PMA, the cells were labeled with 1 µCi of [14C-methyl]choline for 24 h. At the end of labeling, the macrophages were scrapped with a rubber policeman and transferred to a new glass tubes. The cells were thoroughly washed with non-radioactive medium and lipids were further extracted and analyzed as described herein above. PC synthesis was expressed in nmol of [14C-methyl]choline incorporated within individual phospholipids/mg of protein.

GlcCer Accumulation in Gba Neurons

Hippocampal neurons from Gba mice (plated at high density) were cultured for 2 days prior to incubation with 10$^6$ cpm of [$^3$H]dihydrosphingosine (11 Ci/mmol) for 24 h, and then chased for a further 24 h in new medium that did not contain [$^3$H]dihydrosphingosine. Lipids were extracted and analyzed as described below. Glycerolipids were degraded by mild alkaline methanolysis (0.6 N NaOH in methanol for 1 h at room temperature). [$^3$H]GlcCer was separated by TLC on a plate pretreated with 1% sodium tetraborate in methanol, using chloroform:methanol:CaCl$_2$ 9.8 mM (60:35:8 v/v/v) as the developing solvent. Lipids were detected by iodine, the bands scraped and radioactivity determined by scintillation counting.

Labeling of Neuronal Lipids with [$^{14}$C]methyl choline

Neurons were incubated for 48 h with 1 µCi [$^{14}$C]methyl choline/ml of culture medium. Subsequently, medium was removed and the neurons were washed 3-times with phosphate-buffered saline. Neurons were removed from the cover slips by scraping with a rubber policeman into 2 ml of cold methanol, and then sonicated. Part of the resulting suspension was used for lipid analysis, part for analysis of the incorporation of total radioactivity into the cells, and part for DNA analysis (see below).

Lipids were extracted by addition of chloroform to obtain a final chloroform/methanol ratio of 1:1 (v/v). The lower phase was dried under $N_2$ and the upper phase was kept for analysis of [$^{14}$C]methyl choline incorporation into water-soluble metabolites. [$^{14}$C]-labeled lipids were mixed with a lipid standard mixture and separated by two-dimensional TLC using tetrahydrofuran/acetone/methanol/water (50:20:40:6, v/v/v/v) as the first developing solvent, followed by chloroform/acetone/methanol/acetic acid/water (50:20:10:15:5, v/v/v/v/v) as the second developing solvent. Phospholipids were visualized as in Dittmer and Lester (Dittmer J C and Lester L. 1964. A simple specific spray for the detection of phospholipids on thin-layer chromatograms. *J. Lipid Res.* 5, 126-127) and subsequently recovered from the TLC plate by scraping silica directly into scintillation vials. One ml of methanol and 5 ml of Optima Gold scintillation fluid (Packard, Downers Groove, Ill.) were added to each vial for scintillation counting, and radioactivity was determined in a Packard 2100 beta radiospectrometer equipped with the Transformed Spectral Index of the External Standard/Automatic Efficiency Control (tSIE/AEC) program for quench correction and counting of double radiolabeled samples.

Water soluble metabolites were analyzed by addition of choline, phosphocholine, and CDP-choline to the upper phase of the Folch extract (Folch J Lees M and Stanley G H S.1957. A simple method for the isolation and purification of total lipids from animal tissues. J Biol Chem 226:497-509), the mixture dried under $N_2$, and the compounds subsequently separated by TLC using 0.9% NaCl/methanol/28% $NH_4OH$ (50:70:5, v/v/v) as the developing solvent. The plate was air-dried, visualized with iodine, and the water-soluble metabolites removed from the silica by scraping into scintillation vials.

In some cases, acetolysis was performed to determine the amount of [$^{14}$C]-radioactivity that remained in the [$^{14}$C]methyl choline head group moiety of [$^{14}$C]PC after 48 h labeling with [$^{14}$C]methyl choline. [$^{14}$C]PC was removed from TLC plates by scraping, eluted from the silica using chloroform/methanol/acetic acid/water (50:39:1:10, v/v/v/v), and subjected to acetolysis. Briefly, 2 ml of acetic anhydride/acetic acid (2:3, v/v) was added to the tubes containing [$^{14}$C]PC, the mixture heated at 140° C. for 16 h, 200 µl of water added to each tube, dried under $N_2$, and separated into aqueous and organic phases. Products from the aqueous phase were separated by TLC using 0.9% NaCl/methanol/28% $NH_4OH$ (50:70:5, v/v/v), and products from the organic phase were separated by TLC using heptane/diisopropyl ether/acetic acid (60:40:3, v/v/v). [$^{14}$C]-Lipids and the [$^{14}$C]-head group polar moieties were analyzed and quantified as above.

DNA and Protein Determination

DNA was determined using a modified fluorimetric procedure. Briefly, methanol was evaporated under $N_2$, and the dried material was re-suspended in 200 µl of assay buffer (10 mM EDTA, 10 mM Tris pH 7.4, 10 mM NaCl) by sonication. Bisbenzimidazole dye was added to the assay mixture to give a final concentration of 0.1 µg/ml. After 2 h in the dark at room temperature, fluorescence was determined using a Gemini SpectraMax (Molecular Devices, Sunnyvale, CA) microplate reader ($\lambda_{ex}$ of 360 nm; $\lambda_{em}$ of 460 nm). Calf thymus DNA was used as standard. Protein was determined by the Bradford procedure using the BioRad Protein Assay Kit.

CCT Assay

Neurons from individual cover slips were washed twice with ice-cold phosphate-buffered saline, and cells removed by scraping into 300 µl of buffer containing 50 mM imidazole, 2 mM EDTA, 150 mM KCl, 6 mM ADP, 0.2 mM phenylmethylsulfonylfluoride, 1 µg/ml pepstatin and 1 µg/ml leupeptin. After brief sonication, an aliquot was removed for DNA determination and 100 µl was used for the CCT assay.

CCT was assayed as described (Weinhold P A and Feldman D A. 1992. Choline-phosphate cytidylyltransferase. *Methods Enzymol.* 209, 248-258), with some minor modifications. The assay was performed in a final volume of 200 µl containing 1.6 mM phosphorylcholine/0.25 µCi [$^{14}$C]methyl phosphorylcholine, 3 mM CTP, 12 mM magnesium acetate, and DOPC liposomes with or without oleic acid and GlcCer or GalCer, as indicated in the figure legends. Liposomes were prepared by sonicating resuspended lipids in the assay buffer at room temperature for 3 min using a sonicator (Sonics & Materials Inc., Newtown, Conn.) fitted with a micro-tip probe set to 750 W output, using 25% of the maximal amplitude and with pulsations of 9.0 sec every 9.2 sec, which gave a translucent liposome preparation with no precipitates. The final concentration of DOPC and oleic acid in the liposomes was 500 µM each. The reaction was terminated after 25 min at 37° C. by addition of 200 µl of 150 mM phosphorylcholine in 10% trichloroacetic acid. CDP-choline was recovered by addition of 2 ml of 6% charcoal in water (w/v). After 30 min at room temperature the charcoal suspension was washed 4 times with water and centrifuged at 1,000 $g_{av}$ for 10 min. The aqueous supernatants were removed and CDP-choline was eluted from the charcoal with 3 washes of water/ethanol/28% $NH_4OH$ (116:188:11, v/v/v). Eluates were pooled and evaporated to dryness under $N_2$. Phosphorylcholine and CDP-choline were added to the tubes and the samples separated by TLC using 0.9% NaCl/methanol/28% $NE_4OH$ (50:70:5, v/v/v) as the developing solvent. Metabolites were identified by iodine, and the CDP-choline spot was scraped into scintillation vials for scintillation counting.

The efficiency of [$^{14}$C]CDP-choline recovered from the charcoal (Weinhold and Feldman, supra) was estimated using different amounts of rat brain homogenate (up to 50 µg of protein), and compared to CDP-choline extraction by partitioning into the upper phase of a Folch extract (see above), which yields quantitative recovery of [$^{14}$C]CDP-choline. Data obtained by the charcoal extraction was subsequently corrected. Despite the loss of CDP-choline during the charcoal extraction, this method was preferred to the partitioning method since it gives lower contamination of the CDP-choline extract and thus a better resolution on TLC. By both methods, CDP-choline formation was linear with respect to protein for up to 50 µg of protein.

When CCT was assayed in rat or mouse brain cortical homogenates (1 g tissue/12.5 ml of buffer), the homogenate was first centrifuged (200 $g_{av}$, 20 min) to remove cell debris. The homogenate was diluted with assay buffer to give a final concentration of 200 µg protein/ml. CCT activity was also assayed using purified rat brain CCT (see below).

CCT Translocation

Brain cortices were removed from Gba mouse embryos on day 17 and homogenized in the CCT assay buffer described above. Tissue debris was removed by centrifugation (200 $g_{av}$, 20 min); note that a small amount of CCT activity was lost during this step, but did not differ between Gba+/+ and Gba−/− brain homogenates (18±2.6% and 22±1.1% of starting activity, respectively). Particulate and cytosolic fractions were subsequently prepared by centrifugation (100,000 $g_{av}$, 60 min). Each fraction was assayed for CCT activity using 10 µg of protein.

Reverse Transcription-Polymerase Chain Reaction

Total cellular RNA was prepared from ~0.5×10[6] neurons grown on 24 mm cover slips using the RNeasy Mini Kit (Qiagen, Hilden, Germany) according to manufacturers' instructions. The reverse transcription-polymerase chain reaction (RT-PCR) was performed using the QIAGEN OneStep RT-PCR kit (Qiagen, Hilden, Germany). Briefly, each reaction contained 10 ng of total RNA, 0.6 µM of primers, 1.6 mM deoxynucleotide triphosphates (0.4 mM each) and 1 µl QIAGEN OneStep RT-PCR Enzyme Mix in the supplied buffer in a total volume of 25 µl. Primers (CCT: 5'-ACTTTAGTAA GCCCTATGTC (SEQ ID NO. 7) and 5'-GATGATGTCTGATGTGGAGA (SEQ ID NO. 8), 34 cycles, annealing temperatures 53° C.; CCT: 5'-TGAAAAACTGACCATTGCTC (SEQ ID NO. 9) and 5'-ACAATTCTGGTGATGATGTC (SEQ ID NO. 10), 30 cycles, annealing temperature 51° C.; glyceraldehyde-3-phosphate dehydrogenase: 5'-TTAGCACCCCTGGC-CAAGG (SEQ ID NO. 11) and 5'- ATTACTCCTT GGAG-GCCATG (SEQ ID NO. 12), 23 cycles, annealing temperature 50° C.) were designed using the MacMolly Tetra program (Sofigene, Berlin, Germany) and were synthesized by the Weizmann Institute Oligonucleotide and Peptide Synthesis facility. Conditions were adjusted to be within the linear phase of PCR and were as follows: reverse transcription at 50° C. for 30 min, hot start at 95° C. for 15 min, cycles (numbers as indicated for the specific primers) at 94° C. for 40 sec, 50-53° C. (annealing temperature as indicated for the specific primers) for 40 sec, 72° C. for 55 sec, and a final extension period at 72° C. for 10 mm, all using a Stratagene RoboCycler Gradient 96 thermocycler (a kind gift of the Crown Genome Center of the Weizmann Institute) with a heated lid (Stratagene, La Jolla, Calif.). PCR products, 9 µl each, were analyzed by electrophoresis in 1.5 % agarose gels.

CCT Purification from Rat Brain

Rat brain CCT was purified by a method similar to that described for rat liver (Weinhold and Feldman, supra; Weinhold P A Rounsifer M E and Feldman D A. 1986. The purification and characterization of CTP:phosphorylcholine cytidylyltransferase from rat liver. J Biol Chem 261:5104-5110). Rat brains (11 g) were isolated from 8-10-week old rats and homogenized in 51 ml of buffer A (50 mM Tris-HCl pH 7.4, 150 mM NaCl, 1 mM EDTA, 2 mM dithiothreitol, 0.025% (w/v) sodium azide, 1 mM phenylmethylsulfonylfluoride). Brain cytosol was prepared by collecting the supernatants obtained after two sequential centrifugation steps at 10,000 $g_{av}$ for 20 min, and 100,000 $g_{av}$ for 1 h. The protein concentration of the cytosol was adjusted to 6 mg/ml with buffer A, egg yolk PC/oleic acid liposomes were added, followed by acid precipitation. The precipitate was re-suspended in 54 ml of buffer A containing 20 mM n-octyl-β-D-glucopyranoside and 1 mM phenylmethylsulfonylfluoride for 30 min at room temperature. After centrifugation (10,000 $g_{av}$, 20 min), the n-octyl-β-D-glucopyranoside extract was loaded onto a DEAE-sepharose CL-6B column that had been previously packed and equilibrated with 300 ml of buffer A. All elution procedures were performed using a flow rate of 40 ml/h. The column was successively washed with 100 ml of buffer A, 300 ml of a gradient of 150 mM to 300 mM NaCl in buffer B (50 mM Tris-HCl pH 7.4, 1 mM EDTA, 2 mM dithiothreitol, 0.025% (w/v) sodium azide), and 150 ml of buffer B containing 300 mM NaCl. CCT was eluted with 70 ml of buffer B containing 400 mM NaCl and 50 mM n-octyl-β-D-glucopyranoside.

The fractions containing CCT activity were pooled, diluted with 4 volumes of buffer A and loaded onto a HTP gel hydroxyapatite column (BioRad) that had previously been equilibrated with 200 ml of buffer A. Elutions were performed at flow rates of 20 ml/hour. The column was sequentially eluted with (i) 150 ml of 150 mM potassium phosphate in buffer A, (ii) 100 ml of 200 mM potassium phosphate in buffer A, (iii) 150 ml of a gradient of 0 to 50 mM n-octyl-β-D-glucopyranoside in buffer A containing 200 mM potassium phosphate, (iv) 75 ml of buffer A containing 50 mM n-octyl-β-D-glucopyranoside and 200 mM potassium phosphate, (v) 60 ml of buffer A containing 100 mM n-octyl-β-D-glucopyranoside and 200 mM potassium phosphate. CCT activity was eluted with 60 ml of buffer A containing 200 mM potassium phosphate and 0.03% Triton X-100. All glassware used in the purification procedure was siliconized with Sigmacote® solution.

Protein was determined on each fraction and CCT was assayed using DOPC/oleic acid liposomes. The fractions containing CCT were pooled and diluted with 4 volumes of buffer B. CCT was concentrated by centrifugation using Centriplus YM-10 centrifugal filter units (Amicon, Bedford, Mass.), and stored at ~80° C. in buffer A containing 0.03% Triton X-100 and 200 mM potassium phosphate, conditions which have been shown to preserve enzyme stability for several months.

SDS-PAGE and Western Blotting

Prior to sodium dodecyl sulfate polyacrylamide gel electrophoresis (SDS-PAGE), CCT was precipitated at 0° C. for 30 min as described (Sanghera J S and Vance D E. 1989. CTP:phosphocholine cytidylyltransferase is a substrate for cAMP-dependent protein kinase in vitro. J Biol Chem 264: 1215-1223) except that 125 µg/ml of sodium deoxycholate was used. Briefly, the precipitate was centrifuged (2,000 $g_{av}$, 20 min), the pellet washed twice with acetone (–20° C.) and re-suspended in sample buffer (43) prior to SDS-PAGE using a 10% separating gel. Protein was detected using the BioRad Silver Staining Kit.

Western blots were performed on purified CCT (100 ng of protein), or on CCT in Gba mouse cortical homogenates (30 µg of protein) after transfer onto nitrocellulose membranes. The membranes were blocked with 5% dry milk for 1 h at room temperature, washed with Tris-buffered saline (150 mM NaCl, 10 mM Tris-HCl pH 8.0, 0.1% Triton X-100) and exposed overnight to anti-CCT antibodies. The anti-CCTα- and anti-CCTβ antibodies (both rabbit polyclonal antisera) were used at dilutions of 1/300 and 1/200 respectively; the anti-CCTβ antibody (B2 epitope) recognizes an epitope common to the $β_1$ and $β_2$ isoforms. An anti-tubulin antibody (Santa Cruz, Calif.) was used to confirm that equal amounts of protein were loaded in each lane. After washing with Tris-buffered saline, blots were incubated with a goat anti-rabbit secondary antibody conjugated to horseradish peroxidase, for 1 h. Bound antibodies were visualized by chemiluminescence using the Pierce SuperSignal ECL detection kit.

Results

GlcCer Accumulation Stimulates [$^{14}$C]PC Synthesis and Axonal Growth

When rat hippocampal neurons are treated with 200 µM CBE, a significant increase in the rate of axonal growth is observed, with axons ~20% longer than their untreated counterparts after 3 days in culture (Schwarz et al., supra). We have now analyzed growth rates of neurons obtained from Gba mice. Similar to CBE-treated rat neurons, cultured Gba−/− hippocampal neurons exhibit significantly longer axons and more axonal branch points than wild type (Gba+/+) neurons (Table 1), supporting our suggestion that it is GlcCer accumulation rather than a non-specific effect of CBE that is responsible for increased axonal growth rates. Indeed, metabolic labeling of Gba neurons with [$^3$H]dihydrosphingosine revealed an ~4-fold increase in [$^3$H]GlcCer accumulation in Gba−/− (21±8 fmol [$^3$H]GlcCer synthesized/ng DNA) compared to Gba+/+ neurons (5±1 fmol [$^3$H]GlcCer synthesized/ng DNA).

TABLE 1

Morphological analysis of Gba neurons

|  | Wild type (Gba+/+) | Gba−/− |
|---|---|---|
| Length of axon plexus (μm) | 361 ± 47 | 471 ± 62** |
| Axonal branch points per cell | 2.02 ± 0.39 | 2.51 ± 0.21* |

Numbers represent means ± SEM from two separate embryos of each genotype in which 50 cells per cover slip were counted. Statistical differences (Students t test) from wild type neurons are indicated (*p < 0.05, **p < 0.001).

Figure 2:
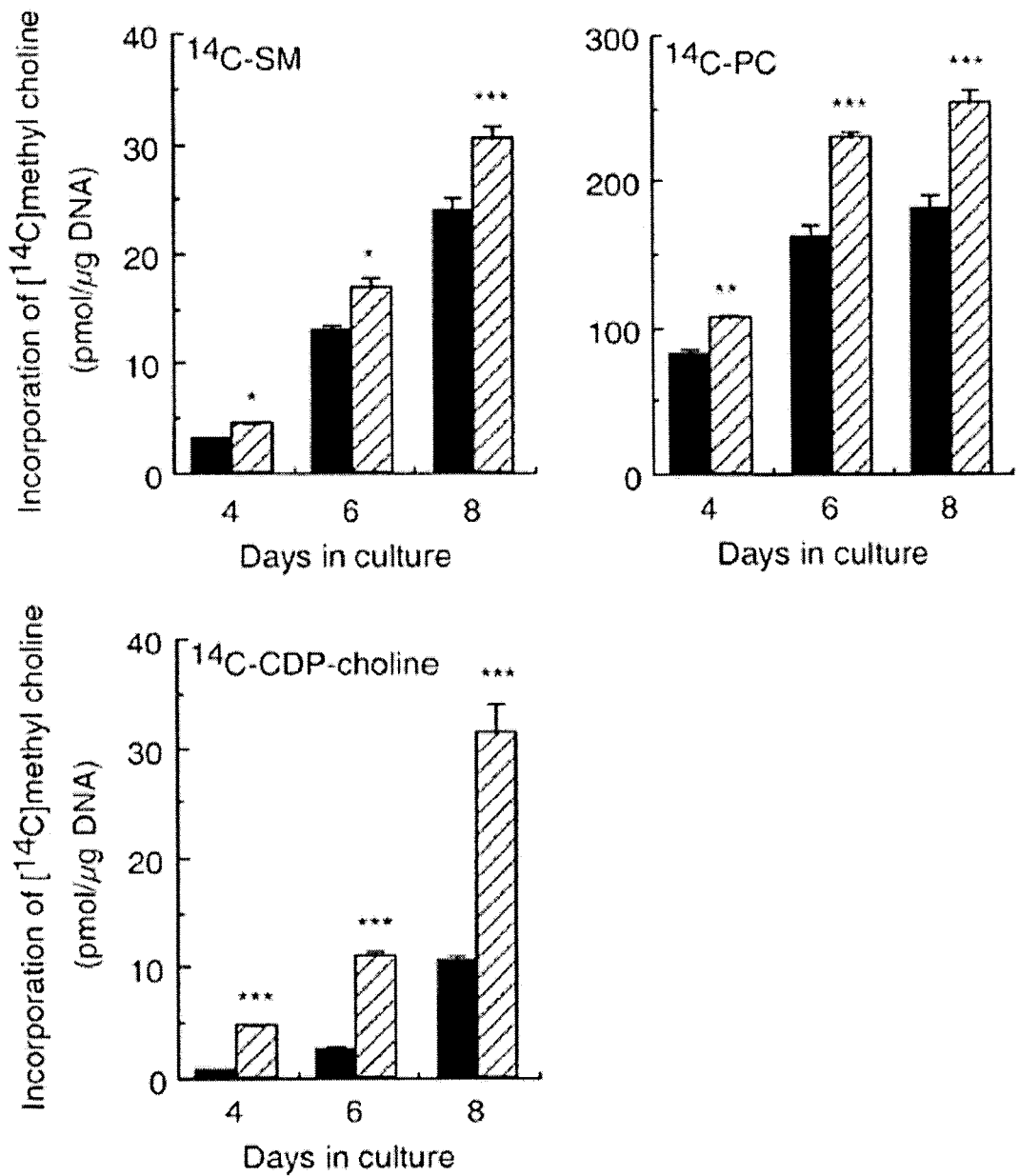
FIG. 2 shows the effect of CBE-treatment on [$^{14}$C] methyl choline incorporation into neuronal lipids. Black bars represent control and stripped bars represent CBE treated cultures. Lipids (sphingomyelin (SM) and PC) and water-soluble metabolites (CDP-choline) were extracted and purified. Results are means ±SEM for 12 individual cover slips taken from 3 separate neuronal cultures. Statistical differences from control neurons are indicated (* $p<0.05$,  $p<0.01$,  $p<0.001$).

The increased growth rates upon intracellular GlcCer accumulation might result in, or be caused by increased rates of phospholipid synthesis, since phospholipids are the major structural components of membranes and are required for axonal growth. To examine this possibility, CBE-treated rat hippocampal neurons, and hippocampal neurons obtained from Gba−/− mice, were incubated with [$^{14}$C]methyl choline to label choline-containing lipids. In CBE-treated neurons, a significant increase in the amount of [$^{14}$C]methyl choline incorporation into the major choline-containing lipids, [$^{14}$C]SM and [$^{14}$C]PC, was observed after 4-days of treatment, and remained elevated for at least 8-days (FIG. 2). Likewise [$^{14}$C]SM and [$^{14}$C]PC synthesis was elevated in Gba−/− neurons compared to Gba+/+ and Gba+/− neurons after 4-days in culture (Table 2). Note that there was no difference in [$^{14}$C]methyl choline incorporation into total tissue (1.60±0.10 nmol/μg DNA for Gba+/+, 1.71±0.04 for Gba+/− and 1.53±0.04 for Gba−/−).

TABLE 2

Incorporation of [$^{14}$C]methyl choline into neuronal lipids from Gba mice

| | $^{14}$C-Lipid synthesis (pmol/μg DNA) | | |
|---|---|---|---|
| | Gba+/+ | Gba+/− | Gba−/− |
| [$^{14}$C]SM | 6.0 ± 0.51 | 6.2 ± 0.2 | 22.1 ± 1.8** |
| [$^{14}$C]PC | 84.0 ± 9.0 | 80.7 ± 1.9 | 170.4 ± 10.4** |
| [$^{14}$C]CDP-choline | 3.6 ± 0.2 | 4.0 ± 0.1 | 5.8 ± 1.0* |
| [$^{14}$C]Phosphorylcholine | 6.0 ± 0.5 | 5.3 ± 0.3 | 3.0 ± 0.5* |

Data are means ± SEM from 9 individual cover slips obtained from 3 embryos taken from 2 different mice litters. Statistical differences from Gba+/+ are indicated (*p < 0.01, **p < 0.001).

Figure 3:
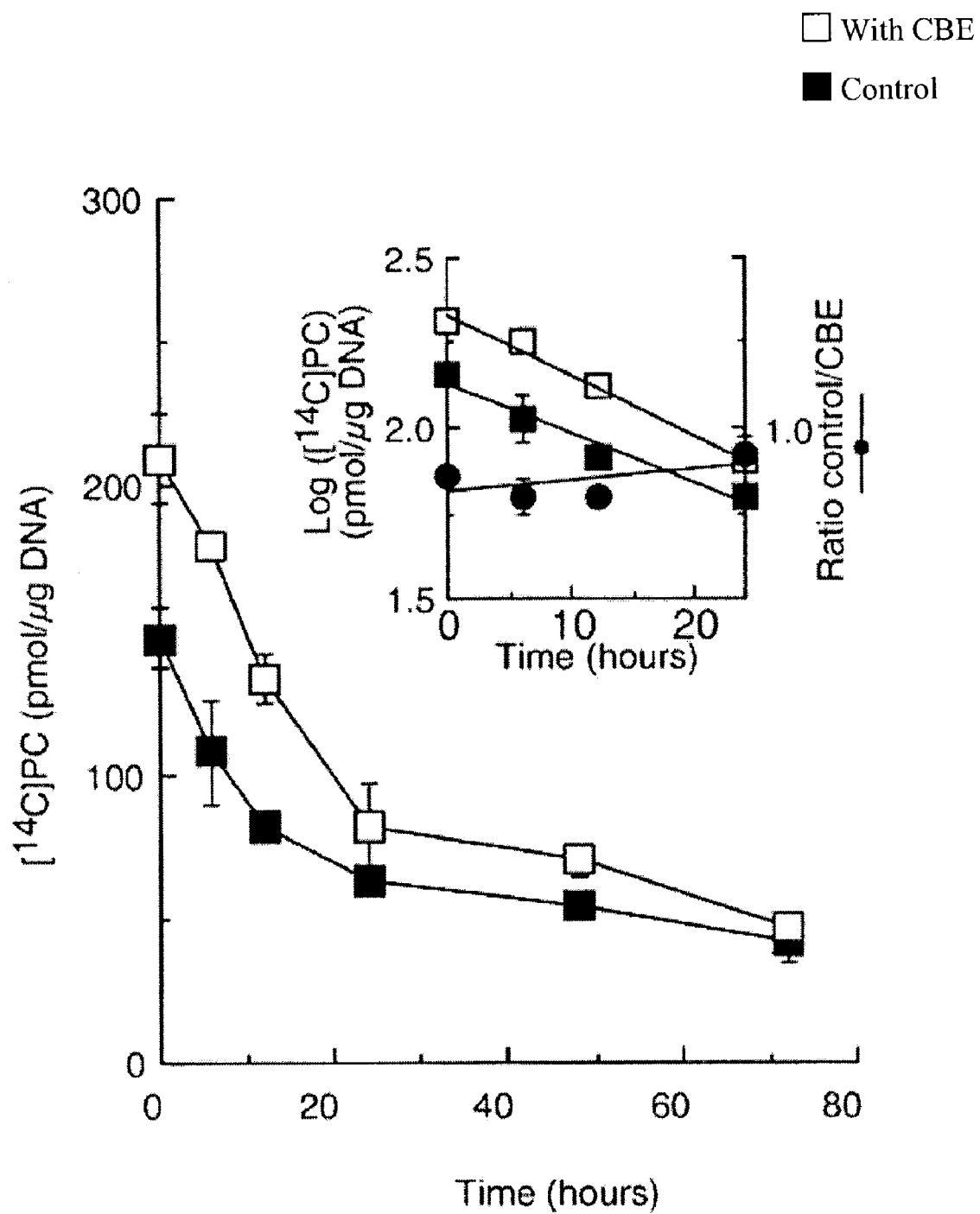
FIG. 3 shows the effect of CBE treatment on [$^{14}$C] phosphatidylcholine (PC) degradation. The insert shows the data plotted on a semi-log scale. Results are means ±SEM from two separate neuronal cultures in which 3 cover slips were analyzed per point. Note that no difference was observed in the rate of degradation when the same data was plotted on a semi-log scale (insert), and no change was observed in the ratio (black circles) of [$^{14}$C]PC levels for control and CBE-treated neurons which remains constant at all time points.

Since metabolic labeling with [$^{14}$C]methyl choline was performed for up to 48 h (due to the relatively low amount of neurons available), we analyzed whether the increase in [$^{14}$C]methyl choline levels was due to changes in the rate of [$^{14}$C]PC synthesis or in the rate of [$^{14}$C]PC degradation. Neurons were incubated with [$^{14}$C]methyl choline to metabolically label [$^{14}$C]PC, and the rate of [$^{14}$C]PC degradation measured. No difference in the rate of degradation between control and CBE-treated neurons was detected (FIG. 3). Moreover, there was no difference in the extent of [$^{14}$C]methyl choline incorporated into the polar head group of [$^{14}$C]PC since 90±2% and 92±3% of the [$^{14}$C]-radioactivity was recovered by acetolysis in the polar head group in control and CBE-treated neurons, respectively.

Analysis of levels of water-soluble metabolites revealed an increase in [$^{14}$C]CDP-choline levels (FIG. 1 and Table 2) and a reduction in [$^{14}$C]phosphorylcholine (Table 2). Together with the lack of change in the rate of [$^{14}$C]PC degradation, these data suggest that CCT, the rate-limiting enzyme in PC synthesis, may be activated in neurons upon GlcCer accumulation.

GlcCer Accumulation Stimulates [$^{14}$C]PC Synthesis in Macrophages

Figure 4:
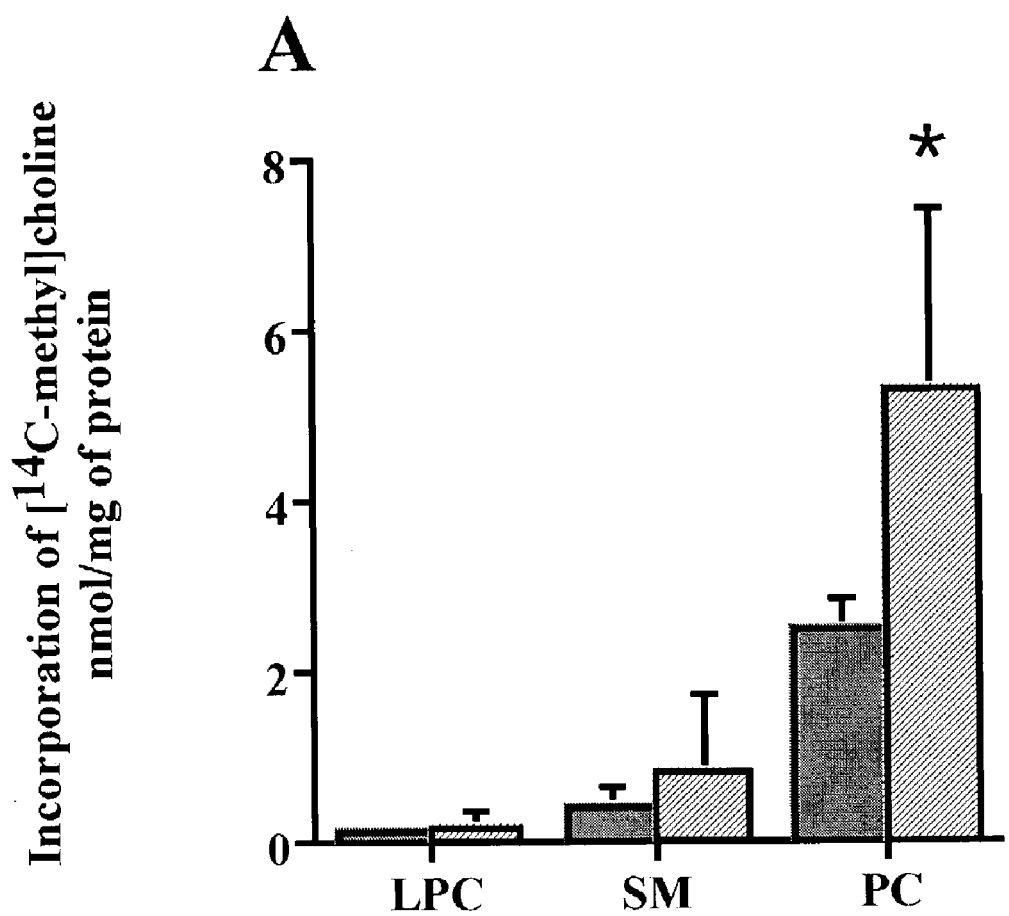
FIG. 4 shows the phospholipid synthesis in CBE treated human macrophages. The black bars represent the control cells while the stripped bars represent the CBE treated cells. Results are expressed in nmol of [$^{14}$C-methyl]choline incorporated within individual phospholipids/mg of protein, and are means ±SD of 5 independent experiments. Statistical differences (Student t-test) are indicated (*: p<0.01).

GlcCer accumulation in human macrophages was obtained by incubating the cultures with 500 μM CBE for 6 days. As CBE inhibits the activity of glucoscerebrosidase, the cells accumulate GlcCer. We now report that PC synthesis and/or turnover is also activated within peripheral blood macrophages accumulating GlcCer. As shown in FIG. 4, a dramatic increase in [$^{14}$C]-PC was observed in the CBE treated macrophages. This observation suggests that, similar to CBE treated rat hippocampal neurons and Gba −/− mouse hippocampal neurons, the CDP-choline pathway for PC synthesis is also elevated in macrophages accumulating GlcCer.

CCT Activity is Up Regulated after GlcCer Accumulation

Figure 5:
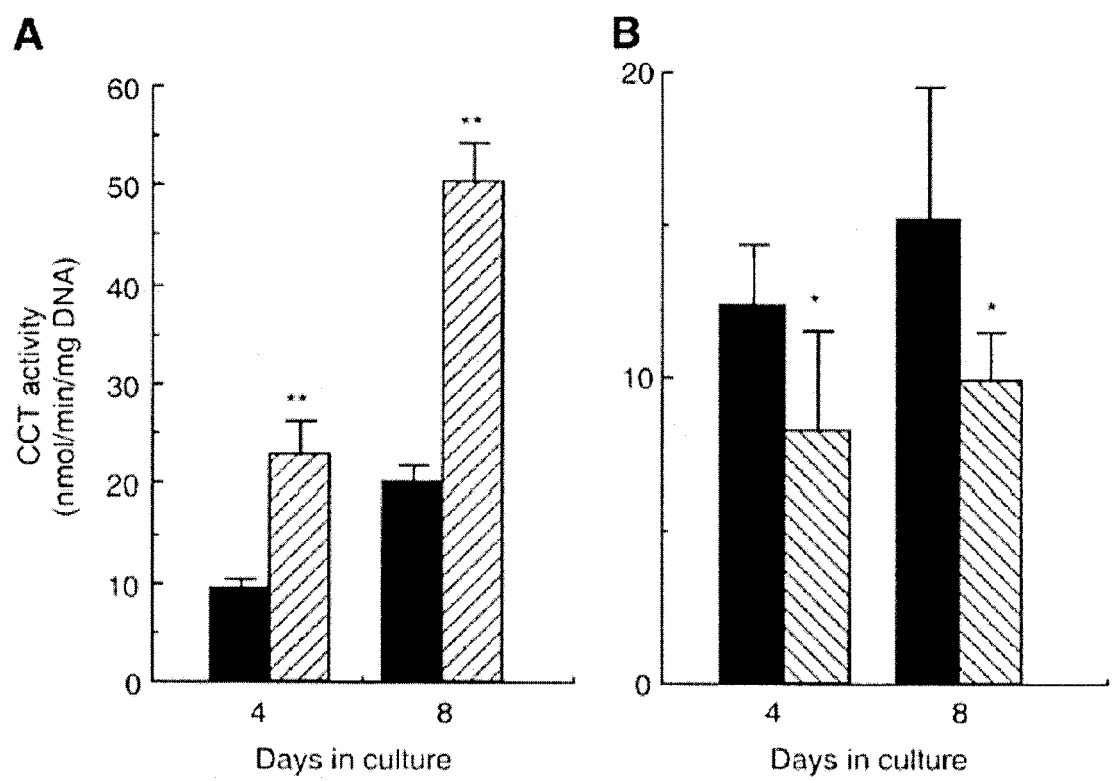
FIG. 5 shows the effect of CBE- and D-threo-1-phenyl-2-decanoyl-amino-3-morpholino-1-propanol (PDMP)-treatment on CCT activity.

To test whether CCT activity is indeed elevated after CBE-treatment, CCT was assayed in homogenates obtained from control and CBE-treated rat hippocampal neurons. A 2-3-fold elevation of CCT activity was detected in neurons that had been incubated with 500 μM CBE for either 4- or 8-days (FIG. 5A), times at which there is a 4-5-fold increase in the rate of incorporation of [$^3$H]dihydrosphingosine into [$^3$H]GlcCer (Korkotian et al., supra); CBE had no effect on CCT activity when added directly to the assay mixture. In contrast, treatment of neurons with 50 μM PDMP, an inhibitor of GlcCer synthesis, resulted in a significant reduction in CCT activity (FIG. 5B), and a reduction in the rate of axonal growth (Schwarz et al., supra).

Figure 6:
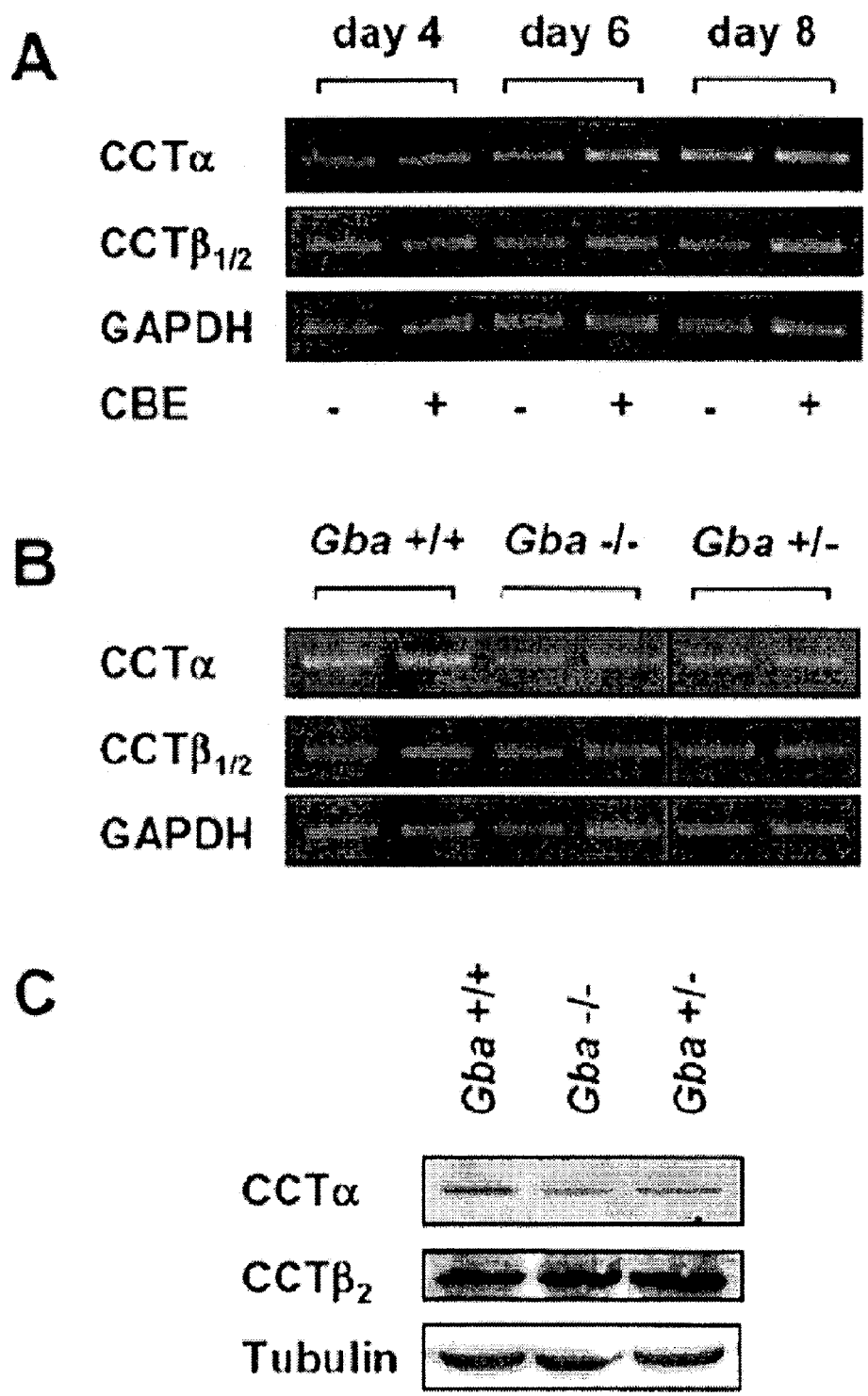
FIG. 6 shows the results of RT-PCR and Western blotting of CCT.

CCT activity can be regulated by transcriptional or post-translational mechanisms (Cornell R B and Northwood I C. 2000. Regulation of CTP:phosphocholine cytidylyltransferase by amphitropism and relocalization. Trends Biochem Sci 25:441-447; Kent C. 1995. Eukaryotic phospholipid biosynthesis. Annu Rev Biochem 64:315-343). To determine whether CCT is transcriptionally up regulated, RT-PCR analysis was performed using primers generated for the α and $β_{1/2}$ CCT isoforms; note that the primers for the $β_{1/2}$ isoforms do not distinguish between the $β_1$ and $β_2$ isoforms as the sequence chosen (see Methods) lies within the non-spliced region of the β isoform. (Note also that a systematic study of the expression of the $β_1$ isoform has not been performed in rodent). No changes in RNA levels could be detected for up to 8-days of CBE-treatment (FIG. 6A), or in Gba−/− (or Gba+/−) compared to Gba+/+ neurons (FIG. 6B). Moreover, no changes in CCT protein levels could be detected in Gba−/− brains compared to Gba+/+ brain by Western blotting using anti-CCTα and anti-CCT$β_{1/2}$ specific antibodies (FIG. 6C).

These results together demonstrate that CCT is not transcriptionally regulated upon GlcCer accumulation.

Figure 7:
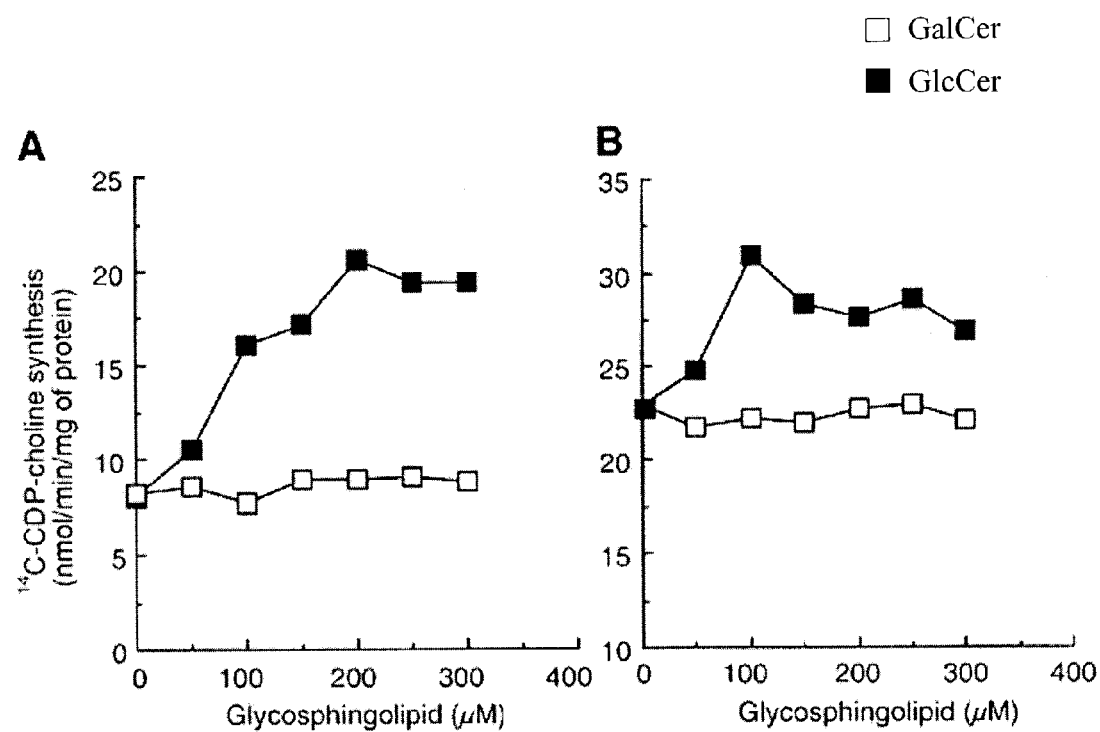
FIG. 7 shows the effect of GlcCer and GalCer on CCT activity in brain homogenates, using lipid mixture consisting of dioleylphosphatidylcholine (DOPC) (FIG. 7A) or DOPC/oleic acid (FIG. 7B). Data are means from two separate experiments in which the variability was <10%.

The effect of exogenously-added GlcCer on CCT activity was examined. Although previous studies examined the effect of cerebrosides on CCT activity (Sohal P S and Cornell R B. 1990. Sphingosine inhibits the activity of rat liver CTP:phosphocholine cytidylyltransferase. J Biol Chem 265:11746-11750), no systematic comparison using different glycosphingolipids, and in particular GlcCer, has been performed. When rat brain cortical homogenates were incubated with DOPC liposomes containing increasing amounts of GlcCer, a dose-dependent increase in the rate of CDP-choline synthesis was observed (FIG. 7A), with >2-fold increase using 200 μM GlcCer. In contrast, GalCer did not affect CCT activity (FIG. 7A), consistent with earlier reports. Likewise, short-acyl chain GlcCer (C8-GlcCer) (200 μM) stimulated CCT activity in DOPC liposomes (CCT activity of 25.9±4.4 nmol/min/mg of protein versus 8.9±1.0 nmol/min/mg with and without C8-GlcCer respectively), whereas C8-GalCer had no effect (9.1±0.8 vs. 8.9±1.0 nmol/min/mg with and without C8-GalCer respectively), demonstrating that the specificity is independent of the fatty acyl composition of GlcCer and GalCer. GlcCer also increased CCT activity when added to liposomes containing a mixture of DOPC and oleic acid, although the effect was far less pronounced than in the absence of oleic acid (FIG. 7B). Again, GalCer had no effect (FIG. 7B). Interestingly, the extent of maximal activation using GlcCer was similar to that of oleic acid, a typical CCT activator, although the dose-dependence of CCT activation by GlcCer was saturable versus concentration (FIG. 7A), similar to that of diacylglycerol (Arnold R S and Cornell R B. 1996. Lipid regulation of CTP: phosphocholine cytidylyltransferase: electrostatic, hydrophobic, and synergistic interactions of anionic phospholipids and diacylglycerol. Biochemistry 35:9917-9924), whereas that of oleic acid is more linear (Sohal and Cornell, supra). Exogenously-added lactosylceramide, SM and ceramide did not increase CCT activity, and no elevation of activity was observed with the lyso-derivatives of these three lipids or with glucosylsphingosine or galactosylsphingosine, although some of them inhibited CCT activity as previously demonstrated (Sohal and Cornell, supra).

Figure 8:
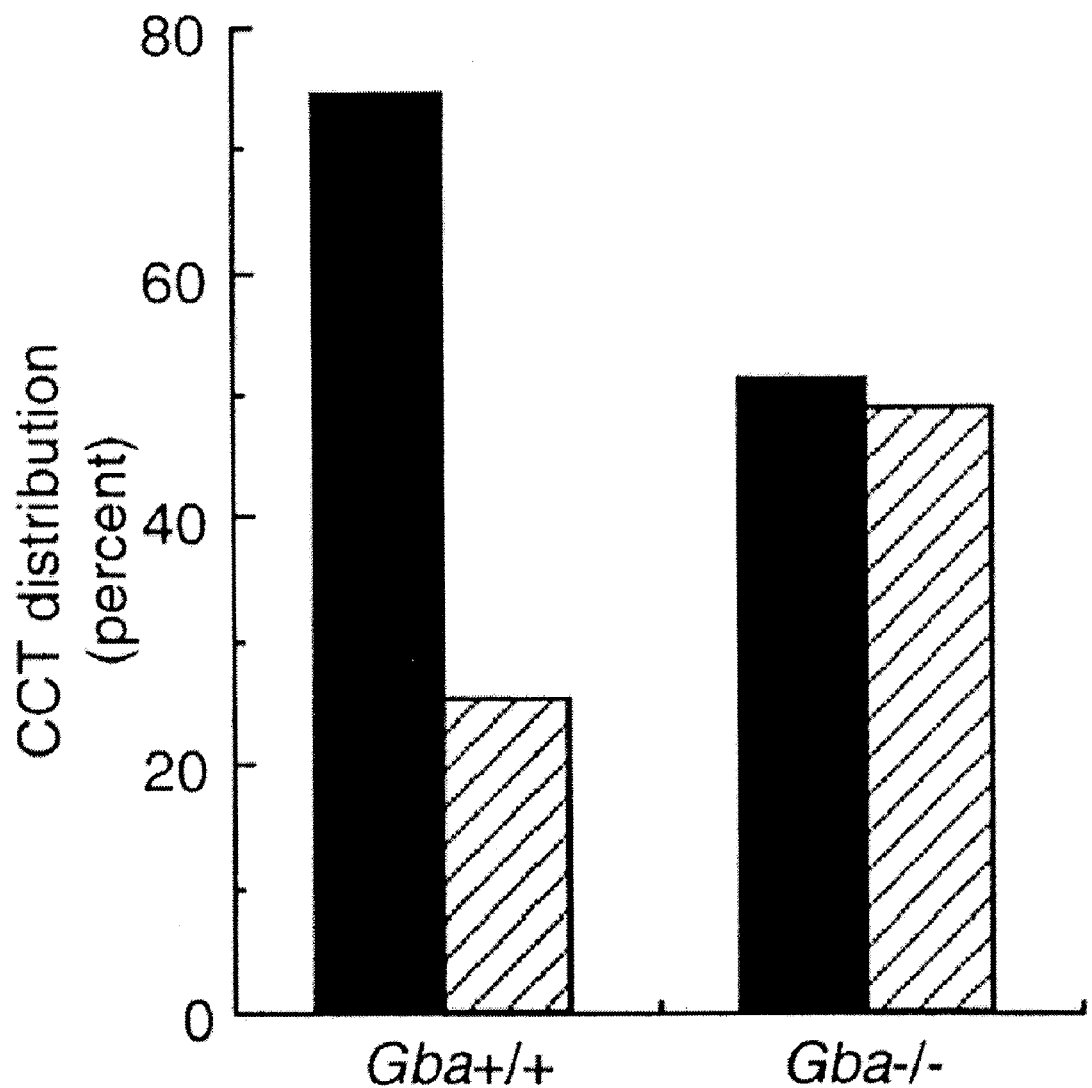
FIG. 8 describes the distribution of CCT activity between cytosol (black bars) and particulate fraction (stripped bars) in homogenates obtained from Gba+/+ and Gba −/− a mouse brain. Data are means of two separate experiments for which similar specific activities (variation of ~10%) were obtained.

One of the major post-translational mechanisms by which CCT is regulated is by altering its distribution between cytosolic and membrane-bound forms (Cornell and Northwood, supra); the latter is significantly more active than the former. Therefore we examined the distribution of CCT activity in homogenates from Gba mouse cortices. Significantly more CCT activity was membrane-associated in Gba−/− brains than in Gba+/+ brains (FIG. 8). Together with the observations above, this data suggests that PC synthesis is up regulated in Gba neurons by GlcCer stimulating the translocation or binding of CCT to membranes.

GlcCer Directly Activates Purified Brain CCT

We have demonstrated that CCT is activated upon intracellular accumulation of GlcCer, and that exogenously added GlcCer can activate CCT in brain homogenates. To determine whether GlcCer activates CCT directly or indirectly, we purified CCT from rat brain, according to procedures developed for rat liver (see Methods). Briefly, this purification scheme involves passing an n-octyl-β-D-glucopyranoside-extract through DEAE-sepharose CL-6B and hydroxyapatite columns. The elution profile of CCT from these columns (FIGS. 9A, B) was similar to that reported for rat liver CCT, except that two additional peaks of activity were eluted from the hydroxyapatite column. An ~1,200-fold purification was obtained (Table 3).

TABLE 3

Purification of rat brain CCT

|  | Total volume (ml) | Total CCT activity (nmol/min) | Total protein (mg) | Specific activity of CCT (nmol/min/mg) | Fold-purification |
|---|---|---|---|---|---|
| Cytosol | 51 | 1308 | 451 | 2.90 | 1 |
| n-octyl-β-D-glucopyranoside extract | 55 | 195 | 39 | 4.93 | 1.7 |
| DEAE-sepharose column | 32 | 91.2 | 0.679 | 134 | 46 |
| Hydroxyapatite column | 56 | 158 | 0.044 | 3,591 | 1,214 |

Figure 9:
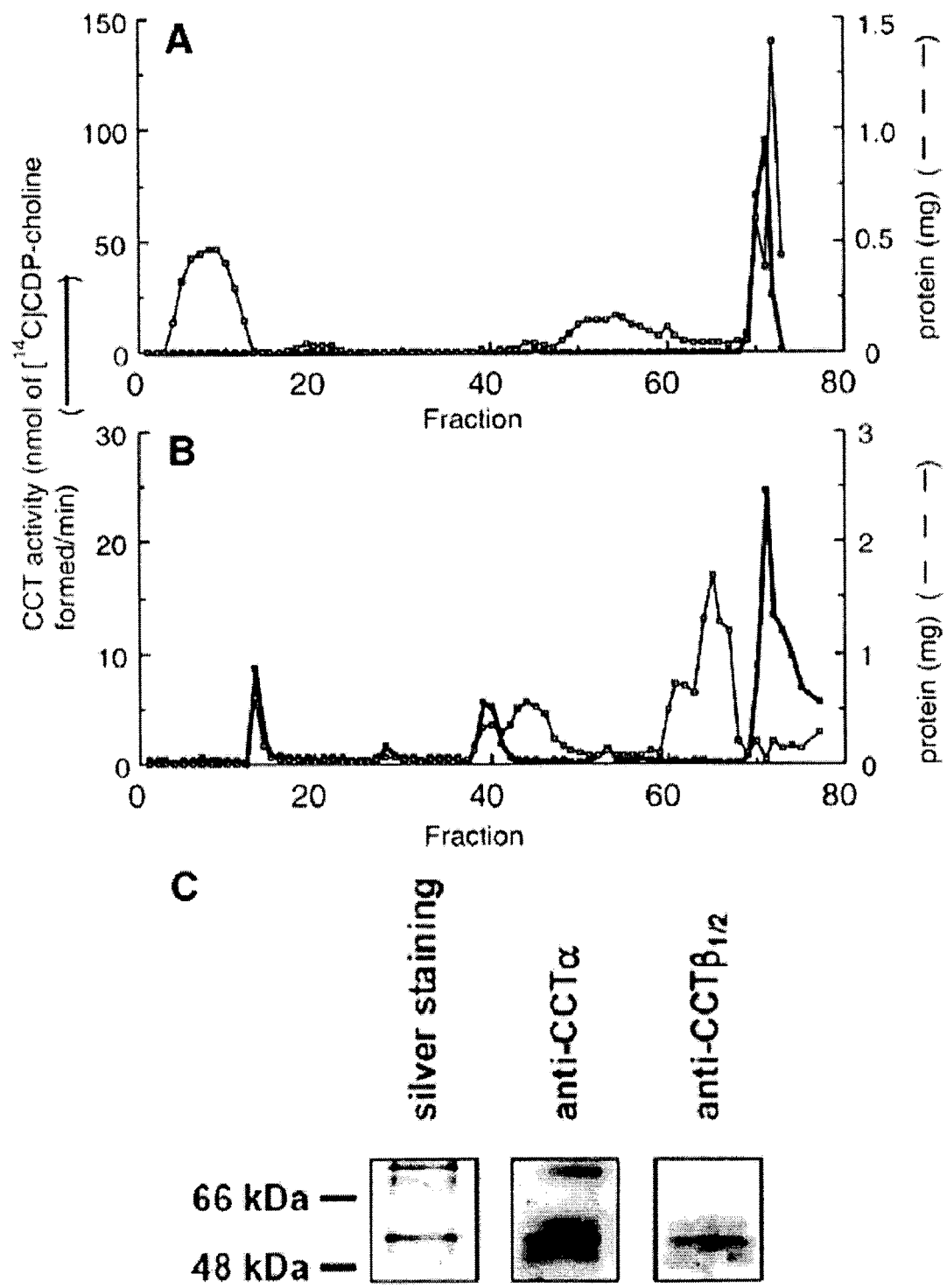
FIG. 9 illustrates CCT purification.

Two prominent bands were obtained by SDS-PAGE with $M_r$ values of ~45-50 kDa and ~80 kDa respectively (FIG. 9C). The ~50 kDa band presumably corresponds to the α and $β_2$ isoforms which overlap at this $M_r$, as it could be recognized by Western blotting using both the anti-α and the anti-$β_{1/2}$ CCT antibodies (FIG. 9C). (The relative molecular mass of the $B_1$ isoform, at least in rat liver, is about 35 kDa and could not be detected in either the purified enzyme preparation, by Western blotting, or by RT-PCR using primers of the (I isoform). The approximate 80 kDa band may indicate dimers of the cc isoform as it was recognized by the anti-α isoform specific antibody but not by the anti-β isoform specific antibody (FIG. 9C).

Figure 10:
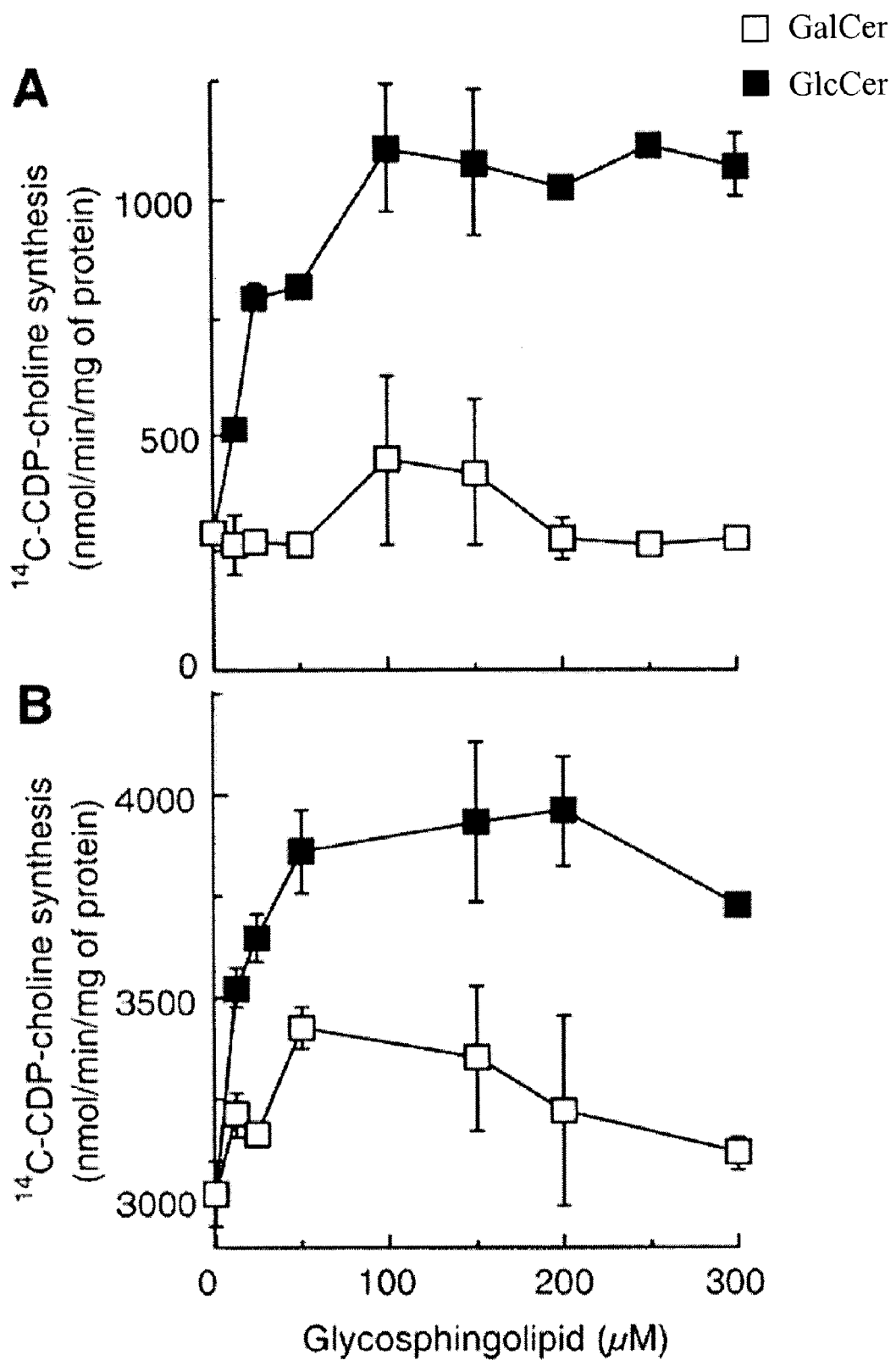
FIG. 10 shows the direct effect of GlcCer and GalCer on purified rat brain CCT, using liposomes consisting of DOPC (FIG. 10A) or DOPC/oleic acid (FIG. 10B). Data are means ±SEM from two independent experiments.

When purified rat brain CCT was incubated with dioleoylphosphatidylcholine (DOPC) liposomes with increasing amounts of GlcCer, a dose-dependent stimulation of CCT activity was observed. A significant activation was detected at the lowest GlcCer concentration (2.5 mole percent of GlcCer), with a maximal 3-4-fold activation at 10 mole percent of GlcCer; no additional activation was seen using higher amounts of GlcCer (FIG. 10A). In contrast, and similar to that observed in rat brain homogenates, GalCer had no significant effect on purified CCT (FIG. 10A). Likewise, a small but significant increase in CCT activity was obtained by including GlcCer in a liposome mixture of DOPC and oleic acid. However, CCT activity was ~10-fold higher in DOPC/oleic acid liposomes than in DOPC liposomes alone, and the level of CCT activation obtained by inclusion of GlcCer in DOPC/oleic acid liposomes was much lower than in liposomes containing DOPC alone (FIG. 10B). Again, no significant effect of GalCer on CCT activity was observed when it was included in DOPC/oleic acid liposome mixtures.

Effect of Sphingolipids and Lyso-Sphingolipids on CCT Activity

Figure 11:
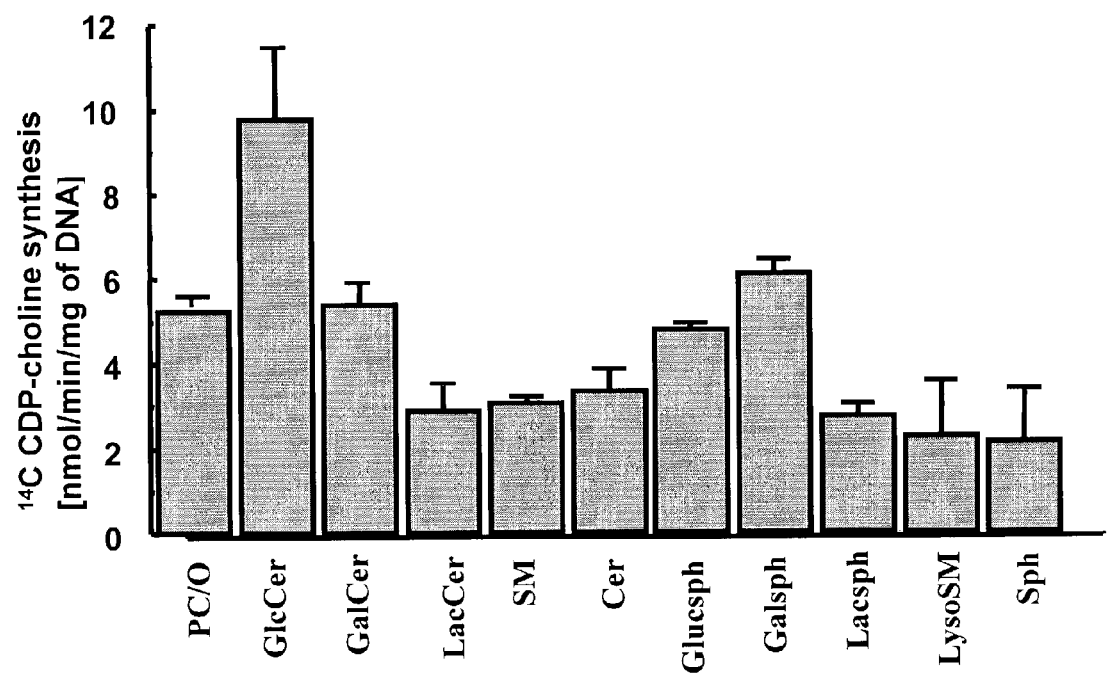
FIG. 11 shows the effect of sphingolipids and lyso-sphingolipid on CCT activity, in homogenates of hippocampal neurons from normal rats.

CCT activity was assayed in homogenates prepared from 8-day-old normal rat hippocampal neurons as described herein above. The reaction mixture comprised 0.5 mM DOPC/0.5 mM oleic acid/0.3 mM sphingolipid or lyso-sphingolipid. CCT activity with each sphingolipid or lyso-sphingolipid was measured twice. Basal CCT activity differed by ~20% between the two experiments; however, the extent of activation or inhibition of CT activity was similar for each sphingolipid and lyso-sphingolipid. As shown in FIG. 11, lactosylceramide (LacCer), sphingomyelin (SM), ceramide (Cer), lactosylsphingosine (LacSph), lysosphingomyelin (LysoSM) and sphingosine (Sph) inhibited CCT activity; as expected, GlcCer activated its activity, and GalCer had no significant effect. No significant effect was also found for glucosylsphingosine and galactosylsphingosine.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. A method of screening for a compound that inhibits deleterious effects due to glucosylceramide (GlcCer) activated phosphatidylcholine (PC) accumulation related to Gaucher disease, the method comprising the steps of:
   a. providing a cell culture in which the cells are overexpressing GlcCer;
   b. exposing the cell culture to at least one candidate compound; and either
   c. measuring the synthesis of PC in the cell culture, wherein a significant decrease in the synthesis of PC as compared to a cell culture incubated without the candidate compound identifies said candidate compound as an inhibitor of PC accumulation; or
   d. measuring the degradation of PC in the cell culture, wherein a significant increase in the degradation of PC as compared to a cell culture incubated without the candidate compound identifies said candidate compound as an inhibitor of PC accumulation.

2. The method according to claim 1 wherein the cell culture is a neuronal cell culture.

3. A method of screening for a compound that inhibits deleterious effects due to glucosylceramide (GlcCer) activated phosphatidylcholine (PC) accumulation related to Gaucher disease, the method comprising the steps of:
   a. providing a cell culture in which the cells are overexpressing GlcCer;
   b. exposing the cell culture to at least one candidate compound; and either
   c. measuring the synthesis of PC in the cell culture, wherein a significant decrease in the synthesis of PC as compared to a cell culture incubated without the candidate compound identifies said candidate compound as an inhibitor of PC accumulation; or
   d. measuring the degradation of PC in the cell culture, wherein a significant increase in the degradation of PC as compared to a cell culture incubated without the candidate compound identifies said candidate compound as an inhibitor of PC accumulation, wherein the cell culture is a macrophage culture.

4. The method according to claim 1 wherein the compound inhibits PC accumulation thereby inhibiting accelerated cell growth.

5. The method according to claim 1 wherein the compound inhibits PC accumulation by inhibiting its synthesis.

6. The method according to claim 5 wherein the compound inhibits PC synthesis by inhibiting the activation of CTP:phosphocholine:cytidylytransferase (CCT) by GlcCer.

7. The method according to claim 5 wherein the compound inhibits PC synthesis by direct inhibition of CCT activity.

* * * * *